United States Patent
Klimko et al.

(10) Patent No.: US 6,552,084 B2
(45) Date of Patent: Apr. 22, 2003

(54) HYDROXYEICOSATETRAENOIC ACID ANALOGS AND METHODS OF THEIR USE IN TREATING DRY EYE DISORDERS

(75) Inventors: Peter G. Klimko, Fort Worth, TX (US); Mark R. Hellberg, Arlington, TX (US); John R. Falck, Dallas, TX (US); Raymond E. Conrow, Crowley, TX (US)

(73) Assignee: Alcon Universal Ltd., Hunenberg (CH)

( * ) Notice: Subject to any disclaimer, the term of this patent is extended or adjusted under 35 U.S.C. 154(b) by 13 days.

(21) Appl. No.: 09/950,457

(22) Filed: Sep. 10, 2001

(65) Prior Publication Data

US 2002/0035095 A1 Mar. 21, 2002

Related U.S. Application Data

(63) Continuation-in-part of application No. 09/694,537, filed on Oct. 23, 2000, now abandoned.
(60) Provisional application No. 60/164,386, filed on Nov. 9, 1999, provisional application No. 60/164,369, filed on Nov. 9, 1999, and provisional application No. 60/164,371, filed on Nov. 9, 1999.

(51) Int. Cl.$^7$ .......................... A01N 37/10; A61K 31/19
(52) U.S. Cl. ................. 514/568; 514/675; 514/690; 514/710; 554/61; 554/213; 564/503; 568/671; 568/687; 568/37
(58) Field of Search ................ 514/558, 640, 514/675, 710; 554/61, 213; 564/503; 568/37, 671, 687

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,421,748 A | 12/1983 | Trager et al. | 424/199 |
| 4,744,980 A | 5/1988 | Holly | 424/78 |
| 4,753,945 A | 6/1988 | Gilbard et al. | 514/263 |
| 4,804,539 A | 2/1989 | Guo et al. | 424/450 |
| 4,818,537 A | 4/1989 | Guo | 424/427 |
| 4,868,154 A | 9/1989 | Gilbard et al. | 514/13 |
| 4,883,658 A | 11/1989 | Holly | 424/80 |
| 4,906,467 A | 3/1990 | Schwartzman et al. | 424/80 |
| 4,914,088 A | 4/1990 | Glonek et al. | 514/76 |
| 4,921,644 A | 5/1990 | Lau et al. | 264/4.1 |
| 4,923,700 A | 5/1990 | Kaufman | 424/427 |
| 4,966,773 A | 10/1990 | Gressel et al. | 424/489 |
| 5,041,434 A | 8/1991 | Lubkin | 514/182 |
| 5,064,655 A | 11/1991 | Uster et al. | 424/450 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | Mackeen | 424/602 |
| 5,294,607 A | 3/1994 | Glonek et al. | 514/76 |
| 5,306,483 A | 4/1994 | Mautone | 424/45 |
| 5,358,706 A | 10/1994 | Marlin et al. | 424/78.04 |
| 5,371,108 A | 12/1994 | Korb et al. | 514/762 |
| 5,389,383 A | 2/1995 | Huth | 424/650 |
| 5,403,598 A | 4/1995 | Beck et al. | 424/717 |
| 5,403,841 A | 4/1995 | Lang et al. | 514/226.8 |
| 5,455,265 A | 10/1995 | Chandraratna | 514/448 |
| 5,578,586 A | 11/1996 | Glonek et al. | 514/76 |
| 5,620,921 A | 4/1997 | Sullivan | 514/178 |
| 5,696,166 A | 12/1997 | Yanni et al. | 514/573 |
| 5,800,807 A | 9/1998 | Hu et al. | 424/78.04 |
| 6,281,192 B1 | 8/2001 | Leahy et al. | 514/8 |

FOREIGN PATENT DOCUMENTS

| | | |
|---|---|---|
| CA | 1 251 736 | 3/1989 |
| EP | 0 097 059 A2 | 12/1983 |
| EP | 0 132 089 A1 | 1/1985 |
| WO | WO 91/12808 | 9/1991 |
| WO | WO 92/04905 | 4/1992 |
| WO | WO 98/16240 | 4/1998 |

OTHER PUBLICATIONS

Alpert et al., "Human Tracheal Epithelial Cells Selectively Incorporate 15–Hydroxyeicosatetraenoic Acid into Phosphatidylinositol," *Am. J. Respir. Cell Mol. Biol.*, vol. 8, pp. 273–281 (1993).

Corfield et al., "Ocular Mucins: Purification, Metabolism and Functions," *Prog Retinal Eye Res.*, vol. 16, pp. 627–656 (1997).

Danjo et al., "Alternation of Mucin in Human Conjunctival Epithelia in Dry Eye," *Invest Ophthalmol Vis. Sci.*, vol. 39; pp. 2602–2609 (1998).

Dartt et. al., Vasoactive intestinal peptide–stimulated glycocongjugate secretion from conjunctival goblet cells. Experimental Eye Research, vol. 63, pp. 27–34, (1996).

Dilly et al., "Surface Changes in the Anesthetic Conjunctiva in Man, with Special Reference to the Production of Mucus from a Non–Goblet–Cell Source," *British Journal of Ophthalmology*, vol. 65; pp. 833–842 (1981).

Dohlman, "Symposium on the Dry Eye, New Concepts in Ocular Xerosis," *Ophthalmological Societies of the United Kingdom*, vol. XCI; pp. 105–118 (1971).

Evans and Sprecher, "Metabolism of ICOSA–5, 11, 14–Trienoic Acid is Human Platelets and the Inhibitor of Arachidonic Acid Metabolism in Human Platelets by ICOSA–5,8,14–Triynoic and ICOSA–5, 11, 14–Triynoic Acids," Prostaglandins, vol. 29(3), pp. 431–441 (1985).

(List continued on next page.)

Primary Examiner—Deborah D. Carr
(74) Attorney, Agent, or Firm—Patrick M. Ryan

(57) ABSTRACT

Hydroxyeicosatetraenoic acid analogs and methods of their use in treating dry eye disorders are disclosed.

24 Claims, No Drawings

OTHER PUBLICATIONS

Glasgow et al., "Tear lipocalins bind a broad array of lipid ligands," *Current Eye Research*, vol. 14(5), pp. 363–372 (1995).

Graber et al., 15–Hydroxyeicosatetraenoic Acid Stimulates Migration of Human Retinal Microvessel Endothelium In Vitro and Neovascularization In Vivo, *Prostaglandins*, vol. 39 (6); pp. 665–673 (1990).

Greiner et al., "Histochemical Analysis of Secretory Vesicles in Non–Goblet Conjunctival Epithelial Cells," *Acta Ophthalmol.*, vol. 63; pp. 89–92 (1985).

Greiner et al., Meibomian gland phospholipids, *Current Eye Research*, vol. 15(4); pp. 371–375 (1996).

Greiner et al., "Mucus Secretory Vesicles in Conjunctival Epithelial Cells of Wearers of Contact Lenses," *Arch Ophthalmol.*, vol. 98; pp. 1843–1846 (1980).

Greiner et al., "Phospholipids in Meibomian Gland Secretion," *Ophthalmic Res.*, vol. 28, pp. 44–49 (1996).

Hamberg et al., "Identification of 15–hydroxy–5.8.11.13–eicosatetraenoic acid (15–HETE) as a major metabolite of arachidonic acid in human lung," *Acta Physiol Scand.*, vol. 110; pp. 219–221 (1980).

Holly et al., "Tear Physiology and Dry Eyes," *Surv. Ophthalmol.*, vol. 22; pp. 69–87 (1977).

Holzfeind et al., "The Human Lacrimal Gland Synthesizes Apolipoprotein D mRNA in Addition to Tear Prealbumin mRNA, Both Species Encoding Members of the Lipocalin Superfamily," *Exp. Eye Res.*, vol. 65, pp. 495–500 (1995).

Hutchinson, "Arachidonate 15–lipoxygenase; characteristics and potential biological significance," *Eicosanoids*, vol. 4, pp. 65–74 (1991).

Inatomi et al., "Human Corneal and Conjunctival Epithelia Express MUC1 Mucin," *Invest Ophthalmol Vis Sci.*, vol. 36; pp. 1818–1827 (1995).

Jansen et al., "Phospholipids Chiral at Phosphorus. Synthesis and Stereospecificity of Phosphorothioate Analogues of Platelet–Activating Factor," *Biochemistry*, vol. 27, pp. 4619–4624 (1988).

Johnson et al., 15–Hydroxyeicosatetraenoic Acid is a Potent Inflammatory Mediator and Agonist of Canine Tracheal Mucus Secretion, from the Hypersensitivity Diseases Research, Lipids Research. The Upjohn Company, Kalamazoo, Michigan, pp. 917–922 (1984).

Kessing et al., "Mucous Gland System of the Conjunctiva," *Acta Ophthalmol. Suppl.*, vol. 95; pp. 1–133 (1968).

Korb et al., Tear Film Lipid Layer Formation: Implications for Contact Lens Wear, *Optometry and Vision Science*, vol. 73(3), pp. 189–192 (1996).

Legrand et al., "Substitution of 15–Hydroxyeicosatetraenoic Acid in the Phosphoinositide Signaling Pathway," *J. of Biological Chemistry*, vol. 266 (12), pp. 7570–7577 (1991).

Lemp et al., "Report of the National Eye Institute/Industry Workshop on Clinical Trials in Dry Eyes," *CLAO*, vol. 21(4), pp. 221–231 (1995).

Lemp, "Tear Substitutes in the Treatment of Dry Eyes," *External Ocular Diseases: Diagnosis and Current Therapy*, Laibson and Trobe (ed.) Little, Brown and Company, Boston; vol. 13(4); pp. 145–153 (1973).

Low et al., "Inhibition of phytohemagglutinin–induced lymphocyte mitogenesis by lipoxygenase metabolites of arachidonic acid: structure–activity relationships," J. or Lipid Research, vol. 25(10); pp. 1090–1095 (1984).

Marom et al., "Effects of Arachidonic Acid, Monohydroxyeicosatetraenoic Acid and Prostaglandins on the Release of Mucous Glycoproteins from Human Airways In Vitro," *The J. of Clinical Investigation*, vol. 67; pp. 1695–1702 (1981).

Marom et al., "Human Airway Monohydroxyeicosatetraenoic Acid Generation and Mucus Release," *Journal of Clinical Investigation*, vol. 72, pp. 122–127 (1983).

Masferrer et al., "12(R)–Hydroxyeicosatetraenoic Acid, An Endogenous corneal Arachidonate Metabolite, Lowers Intraocular Pressure in Rabbits," *Investigative Ophthalmology and Visual Science*, vol. 31(3); pp. 535–539 (1990).

McCulley et al., "Tear Film Structure and Dry Eye," *Contactologia*, vol. 20, pp. 145–149 (1998).

Midland et al., "Asymmetric Reductions of Propargyl Ketones," *Tetrahedron*, vol. 40(8), pp. 1371–1380 (1984).

Mysore et al., "Controlled Ocular Drug Delivery and Vesicular Systems: An Overview," *Indian Drugs*, vol. 33(9), pp. 431–442 (1996).

Nakamura et al., "Gefarnate stimulates secretion of mucin–like glycoproteins by corneal epithelium in vitro and protects corneal epithelium from dessication in vivo," *Expiremental Eye Research*, vol. 65, pp. 569–574 (1997).

Ohno, M.; Otsuka, M. Organic Reactions, vol. 37, p. 1 (1989).

Ohyama et al., "Sensitive Densitometry for the Determination of Platelet–activating Factor and Other Phospholipids in Human Tears," *Analyst*, vol. 121, pp. 1943–1947 (1996).

Petrich et al., "The suppresssion of 5–lipoxygenation of arachidonic acid in human polymorphonuclear leucocytes by the 15–lipoxygenase product(15S)–hydroxy–(5Z, 8Z, 11Z, 13E)–eicosatetraenoic aicd: structure–activity relationship and mechanism of action," Biochemical Journal, vol. 314(3), pp. 911–916 (1996).

Pleyer et al., "Analysis of Interactions Between the Corneal Epithelium and Liposomes" Qualitative and Quantitative Fluorescence Studies of a Corneal Epithelial Cell Line, *Survey of Ophthalmology.*, vol. 39 (Supl. 1), S3–S16 (1995).

Profita et al., "Interleukin–4 Enhances 15–Lipoxygenase Activity and Incorporation of 15(S)–HETE into Cellular Phospholipids in Cultured Pulmonary Epithelial Cells," *Am. J. Respir. Cell Mol. Biol.*, vol. 20, pp. 61–68 (1999).

Prydal et al., "Study of Human Tear Film Thickness and Structure Using Laser Interferometry," *Invest Ophthalmol Vis Sci.*, vol. 33; pp. 2006–2011 (1992).

Shelhamer et al., "The Effects of Arachinoids and Leukotrienes on the Release of Mucus from Human Airways," *Chest Supplement*, 24th Aspen Lung Conference, vol. 81(5); pp. 36S–37S (1982).

Shigemitsu et al., "Effects of Mucin Ophthalmic Solution on Epithelial Wound Healing in Rabbit Cornea," *Ophthalmic Res.*, vol. 29; pp. 61–66 (1997).

Shine et al., Keratoconjunctivitis Sicca Associated with Meibomian Secretion Polar Lipid Abnormality, *Arch. Ophthalmology*, vol. 116, pp. 849–852 (1998).

Steffenrud et al., "Gas Chromatography–mass Spectrometry of Monohydroxyeicosatetraenoic Acids as Their Methyl Esters Trimetylsilyl, allyldimethylsilyl and tert. –butyldimethylsilyl ethers," J. of Chromatography, vol. 416(2), pp. 219–235 (1987).

Watanabe et al., "Human Corneal and Conjunctival Epithelia Produce a Mucin–like Glycoprotein for the Apical Surface," *Invest Ophthalmol Vis Sci.*, vol. 36; pp. 337–344 (1995).

Wiggins et al., "12(S)–Hydroxy–5,8. 10. 14–Eicosatetraenoic Acid is a More Potent Neutrophil Chemoattractant Than the 12(R) Epimer in the Rat Cornea," *Prostaglandins*, vol. 49(2) pp. 131–141 (1990).

Yanni et al., "Effect of Intravenously Administered Lipoxygenase Metabolites on Rat Tracheal Mucous Gel Layer Thickness," *Int Arch Allergy Appl Immunol*, vol. 90 pp. 307–309 (1989).

Yu et al., "Effect of Polar Head Groups on the Interactions of Phospholipase $A_2$ with Phosphonate Transition–State Analogues," *Biochemistry*, vol. 32, pp. 10185–10192.

Zhang et al., "Enzymatic Asymmetric Hydroxylation of Pentadienols Using Soybean Lipoxygenase," *J. Am. Chem. Soc.*, vol. 111(26), pp. 9241–9242 (1989).

Zhu et al., Synthesis of Phospholipids Bearing a Conjugated Oxo–polyunsaturated Fatty Acid Residue, *J. Chem. Research* (S)., vol. 8, pp. 500–501 (1999).

HYDROXYEICOSATETRAENOIC ACID ANALOGS AND METHODS OF THEIR USE IN TREATING DRY EYE DISORDERS

This application is a continuation-in-part application of U.S. application Ser. No. 09/694,537, filed Oct. 23, 2000, now abandoned, which claims the benefit of U.S. Provisional Applications, U.S. Ser. No. 60/164,386 filed Nov. 9, 1999; U.S. Ser. No. 60/164,369 filed Nov. 9, 1999, and U.S. Ser. No. 60/164,371 filed Nov. 9, 1999.

The present invention is directed to compositions containing hydroxyeicosatetraenoic acid analogs and methods for their use in treating dry eye.

BACKGROUND OF THE INVENTION

Dry eye, also known generically as *keratoconjunctivitis sicca*, is a common ophthalmological disorder affecting millions of Americans each year (Schein et. al., *Prevalence of dry eye among the elderly. American J. Ophthalmology*, 124:723–738, (1997)). The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eyelid and the eye surface. In severe cases, vision may be substantially impaired. Other diseases, such as Sjogren's disease and *cicatricial pemphigoid* manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the Nation Eye Institute/Industry Workshop on Clinical Trials in Dry Eyes, The CLAO Journal*, volume 21, number 4, pages 221–231 (1995)). Four events have been identified which singly or in combination are believed to result in the dry eye condition: a) decreased tear production or increased tear evaporation; b) decreased conjunctival goblet-cell density; c) increased corneal desquamation; and d) destabilization of the cornea-tear interface (Gilbard, *Dry eye: pharmacological approaches, effects, and progress. The CLAO Journal*, 22:141–145 (1996)). Another major problem is the decreased mucin production by the conjunctival cells and/or corneal epithelial cells of mucin, which protects and lubricates the ocular surface (Gipson and Inatomi, *Mucin genes expressed by ocular surface epithelium. Progress in Retinal and Eye Research*, 16:81–98 (1997)).

Practitioners have taken several approaches to the treatment of dry eye. One common approach has been to supplement and stabilize the ocular tear film using so-called artificial tears instilled throughout the day. Another approach has been the use of ocular inserts that provide a tear substitute or to stimulate endogenous tear production.

Examples of the tear substitution approach include the use of buffered, isotonic saline solutions, aqueous solutions containing water-soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. Nos. 4,131,651 (Shah et al.), 4,370,325 (Packman), 4,409,205 (Shively), 4,744,980 and 4,883,658 (Holly), 4,914,088 (Glonek), 5,075,104 (Gressel et al.) and 5,294,607 (Glonek et al.).

United States Patents directed to the use of ocular inserts in the treatment of dry eye include U.S. Pat. No. 3,991,759 (Urquhart). Other semi-solid therapy has included the administration of carrageenans (U.S. Pat. No. 5,403,841, Lang) which gel upon contact with naturally occurring tear film.

Another recent approach involves the provision of lubricating substances in lieu of artificial tears. U.S. Pat. No. 4,818,537 (Guo) discloses the use of a lubricating, liposome-based composition.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate preocular tear film; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective treatment for dry eye that is capable of alleviating symptoms, as well as treating the underlying physical and physiological deficiencies of dry eye, and that is both convenient and inexpensive to administer.

Mucins are proteins that are heavily glycosylated with glucosamine-based moieties. Mucins provide protective and lubricating effects to epithelial cells, especially those of mucosal membranes. Mucins have been shown to be secreted by vesicles and discharged on the surface of the conjunctival epithelium of human eyes (Greiner et al., *Mucus Secretory Vesicles in Conjunctival Epithelial Cells of Wearers of Contact Lenses, Archives of Ophthalmology*, volume 98, pages 1843–1846 (1980); and Dilly et al., *Surface Changes in the Anaesthetic Conjunctiva in Man, with Special Reference to the Production of Mucus from a Non-Goblet-Cell Source, British Journal of Ophthalmolog*, volume 65, pages 833–842 (1981)). A number of human-derived mucins which reside in the apical and subapical corneal epithelium have been discovered and cloned (Watanabe et al., *Human Corneal and conjunctival Epithelia Produce a Mucin-Like Glycoprotein for the Apical Surface, Investigative Ophthalmology and Visual Science*, volume 36, number 2, pages 337–344 (1995)). Recently, Watanabe discovered a new mucin which is secreted via the cornea apical and subapical cells as well as the conjunctival epithelium of the human eye (Watanabe et al., *IOVS*, volume 36, number 2, pages 337–344 (1995)). These mucins provide lubrication, and additionally attract and hold moisture and sebaceous material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al, *Effect of Intravenously Administered Lipoxygenase Metabolites on Rat Tracheal Mucous Gel Layer Thickness, International Archives of Allergy And Applied Immunology*, volume 90, pages 307–309 (1989)). Similarly, Marom has reported the production of mucosal glycoproteins in human lung by HETE derivatives (Marom et al., *Human Airway Monohydroxyeicosatetraenoic Acid Generation and Mucus Release, Journal of Clinical Investigation*, volume 72, pages 122–127 (1983)). Nowhere in the art, however, has the use of HETE derivatives been proposed to stimulate mucin production in ocular tissues as a treatment for dry eye.

The conventional treatment for dry eye, as discussed above, includes administration of artificial tears to the eye several times a day. Other agents claimed for increasing ocular mucin and/or tear production include vasoactive intestinal polypeptide (Dartt et. al., *Vasoactive intestinal peptide-stimulated glycoconjugate secretion from conjunctival goblet cells. Experimental Eye Research*, 63:27–34, (1996)), gefarnate (Nakmura et. al., *Gefarnate stimulates secretion of mucin-like glycoproteins by corneal epithelium in vitro and protects corneal epithelium from desiccation in vivo, Experimental Eye Research*, 65:569–574 (1997)), and the use of liposomes (U.S. Pat. No. 4,818,537), androgens (U.S. Pat. No. 5,620,921), melanocyte stimulating hormones (U.S. Pat. No. 4,868,154), and phosphodiesterase inhibitors (U.S. Pat. No. 4,753,945), retinoids (U.S. Pat. No. 5,455,265). However, many of these compounds or treatments suffer from a lack of specificity, efficacy and potency and none of these agents have been marketed so far as therapeutically useful products to treat dry eye and related ocular surface diseases. Of particular relevance to the present invention is the claimed use of hydroxyeicosatetraenoic acid derivatives to treat dry eye (U.S. Pat. No. 5,696,166). Thus, there remains a need for an efficacious therapy for the treatment of dry eye and related diseases.

SUMMARY OF THE INVENTION

The present invention is directed to compositions and methods for the treatment of dry eye and other disorders requiring the wetting of the eye. More specifically, the present invention discloses analogs of (5Z,8Z,11Z,13E)-15-hydroxyeicosa-5,8,11,14-tetraenoic acid (15-HETE) and methods using the same for treating dry eye type disorders. The compositions are administered topically to the eye for the treatment of dry eye.

DETAILED DESCRIPTION OF THE INVENTION

It has now been discovered that certain 15-HETE analogs are useful in treating dry eye or other disorders requiring the wetting of the eye. It is believed that such analogs stimulate mucin production in human conjunctival epithelium. These compounds are of formula I:

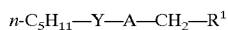

wherein:

$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:

R is H or a pharmaceutically acceptable cation, or $CO_2R$ forms a pharmaceutically acceptable ester moiety;

$NR^2R^3$, $NR^5R^6$ are the same or different and comprise a free or functionally modified amino group;

$OR^4$ comprises a free or functionally modified hydroxy group;

Hal is F, Cl, Br, or I;

$R^{20}$ is H, alkyl, acyl;

$R^{21}$ is H or a pharmaceutically acceptable cation, or $COSR^{21}$ forms a pharmaceutically acceptable thioester moiety;

A is $L_1$—$A_1$—$L_2$, $L_1$—$A_2$—$L_2$, $L_3$—$A_2$—$L_4$, or $L_5$—$A_2$—$L_3$;

$A_1$ is $CH_2CH_2$;

$A_2$ is

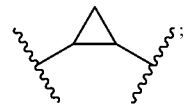

$L_1$ is $CH_2$—B—D;

B and D are the same or different and are $CH_2CH_2$, CH=CH, or C≡C;

$L_2$ is $CH_2$—K—$CH_2CH_2$;

K is $CH_2CH_2$, CH=CH, or C≡C;

$L_3$ is $CH_2CH_2CH_2$, $CH_2CH$=CH, $CH_2C$≡C, CH=CHCH_2, C≡CCH_2, or CH=C=CH;

$L_4$ is X—$CH_2CH_2$;

X is $CH_2CH_2CH$=CH, $CH_2CH_2C$≡C, $CH_2CH_2CH_2CH_2$, $CH_2CH$=CHCH_2, $CH_2C$≡CCH_2, CH=CHCH_2CH_2, C≡CCH_2CH_2, $CH_2CH$=C=CH, or CH=C=CHCH_2;

$L_5$ is $CH_2CH_2$—B—D; and

Y is C(O) (i.e. a carbonyl group) or Y is

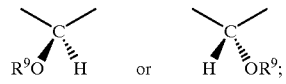

wherein $R^9O$ constitutes a free or functionally modified hydroxy group.

Except for those compounds of formula I with $A_1$=$CH_2CH_2$, all of the compounds of the present invention are believed to be novel.

The compounds of formula I may also be incorporated into phospholipids as glyceryl esters or sphingomyelin amides. Phospholipid sphingomyelin amides of the compounds of formula I will typically comprise a formula I compound amidated via its carbon 1 carboxylate to the amino group of the sphingomyelin backbone. The phospholipid formula I esters will comprise various phospholipids. Phospholipid esters of the compounds of formula I will typically comprise a formula I compound esterified via its carbon 1 carboxylate to the sn-1 or sn-2 position alcohol, or both, of the glycerol backbone of the phospholipid. If the sn-1 or sn-2 position of the glyceryl ester class does not contain an ester of a compound of formula I, then such carbon positions of the glycerol backbone will comprise a methylene, ether or ester moiety linked to a substituted or unsubstituted $C_{12-30}$ alkyl or alkenyl (the alkenyl group containing one or more double bonds); alkyl(cycloalkyl)alkyl; alkyl(cycloalkyl); alkyl(heteroaryl); alkyl(heteroaryl)alkyl; or alkyl-M—Q; wherein the substitution is alkyl, halo, hydroxy, or functionally modified hydroxy; M is O or S; and Q is H, alkyl, alkyl(cycloalkyl)alkyl, alkyl(cycloalkyl), alkyl (heteroaryl) or alkyl(heteroaryl)alkyl. However, at least one of the sn-1 or sn-2 position alcohols of the glycerol backbone must form an ester with a compound of formula I via the carbon 1 carboxylate of the latter. Preferred phospholipid-formula I) esters will be of the phosphatidylethanolamine, phosphatidylcholine, phosphatidylserine, and phospatidylinositol type. The most preferred phospholipid-formula I esters will comprise a formula I compound esterified via its carbon 1 carboxylate to the alcohol at the sn-2 position of phosphatidylcholine, phosphatidylethanolamine or phosphatidylinositol. The phospholipid-formula I esters and sphingomyelin amides may be synthesized using various phospholipid synthetic methods known in the art; see for example, Tsai et al., *Biochemistry*, volume 27, page 4619 (1988); and Dennis et al., *Biochemistry*, volume 32, page 10185 (1993).

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis;* J. D. Morrison and J. W. Scott, Eds.; Academic Press Publishers: New York, 1983–1985, volumes 1–5; *Principles of Asymmetric Synthesis;* R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC;* G. Subramanian, Ed.; VCH Publishers: New York, 1994; *Chiral Separations by HPLC;* A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

As used herein, the terms "pharmaceutically acceptable salt" and "pharmaceutically acceptable ester" means any salt or ester, respectively, that would be suitable for therapeutic administration to a patient by any conventional means without significant deleterious health consequences; and "ophthalmically acceptable salt" and "ophthalmically acceptable ester" means any pharmaceutically acceptable salt or ester, respectively, that would be suitable for ophthalmic application, i.e. non-toxic and non-irritating.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-, heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, $NHOH$, and $NH(OCH_3)$.

The term "free thiol group" means an SH. The term "functionally modified thiol group" means an SH which has been functionalized to form: a thioether, where an alkyl, aryl, cycloalkyl, heterocycloalkyl, alkenyl, cycloalkenyl, heterocycloalkenyl, alkynyl, or heteroaryl group is substituted for the hydrogen; or a thioester, in which an acyl group is substituted for the hydrogen. Preferred moieties include SH, $SC(O)CH_3$, $SCH_3$, $SC_2H_5$, $SCH_2C(O)C_2H_5$, and $SCH_2C(O)CH_3$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "heterocycloalkyl" refers to cycloalkyl rings that contain at least one heteroatom such as 0, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 15 carbon atoms with at least one carbon—carbon double bond, the chain being optionally interrupted by one or more heteroatoms. The chain hydrogens may be substituted with other groups, such as halogen. Preferred straight or branched alkeny groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon—carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$-$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group bonded from its oxygen atom to the carbon of a carbonyl group, the carbonyl group itself being bonded to another atom through its carbon atom.

Preferred compounds of the present invention include those of formula I, wherein:

$R^1$ is $CO_2R$, where R is H or an ophthalmically acceptable cationic salt, or $CO_2R$ forms an ophthalmically acceptable ester moiety;

A is $L_1$—$A_1$—$L_2$ or L—$A_2$—$L_2$;
$A_1$ is $CH_2CH_2$;
$A_2$ is

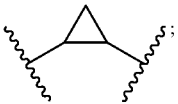

$L_1$ is $CH_2$—B—D;
$L_2$ is $CH_2$—K—$CH_2CH_2$;
B is C≡C or cis-CH═CH and D is C≡C or trans-CH═CH;
K is cis-CH═CH; and
Y is

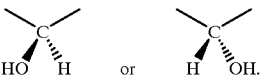

Other preferred compounds of the present invention include those of formula I, wherein:

$R^1$ is $CO_2R$, where R is H or an ophthalmically acceptable cationic salt, or $CO_2R$ forms an ophthalmically acceptable ester moiety;

A is $L_3$—$A_2$—$L_4$;
$A_2$ is

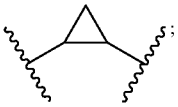

$L_3$ is trans-$CH_2CH$═CH, trans-CH═$CHCH_2$, or $CH_2C$≡C;
$L_4$ is X—$CH_2CH_2$;
X is cis-$CH_2CH_2CH$═CH, $CH_2CH_2C$≡C, cis-$CH_2CH$═$CHCH_2$, or cis CH═$CHCH_2CH_2$;
Y is

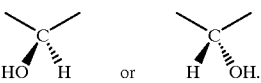

Still other preferred compounds of the present invention include those of formula I, wherein:

$R^1$ is $CO_2R$, where R is H or an ophthalmically acceptable cationic salt, or $CO_2R$ forms an ophthalmically acceptable ester moiety;

A is $L_5$—$A_2$—$L_3$;
$A_2$ is

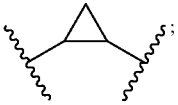

$L_5$ is $CH_2CH_2$—B—D;
$L_3$ is cis-$CH_2CH$═CH, cis-CH═$CHCH_2$, $CH_2C$≡C, or $CH_2CH_2CH_2$;
B is cis-CH═CH or C≡C;
D is trans-CH═CH or C≡C; and Y is

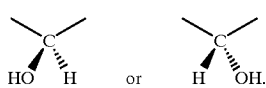

Among the especially preferred of the foregoing compounds are those whose preparations are detailed in the following examples 1–19.

EXAMPLE 1

Synthesis of 1

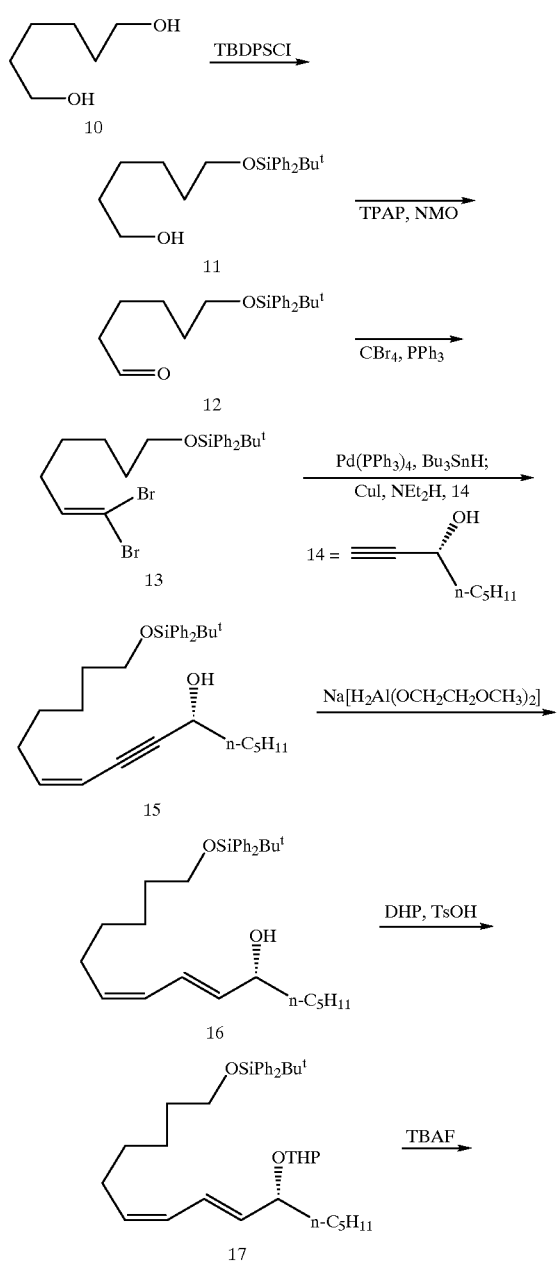

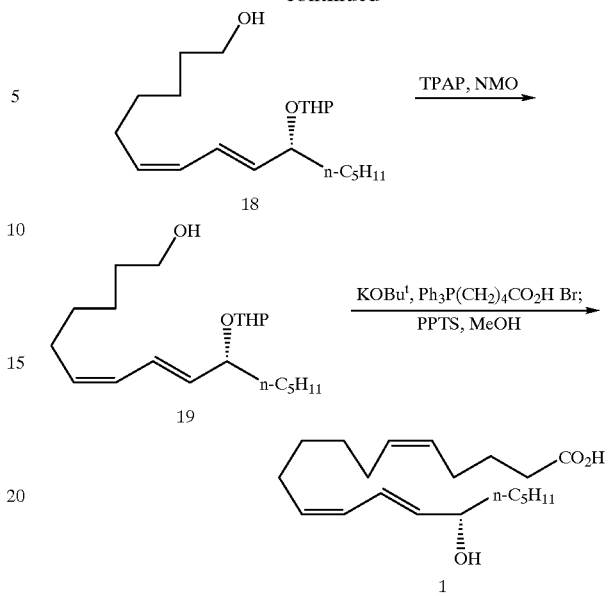

Compound 1

Treatment of 1,6-hexanediol (10) with 0.9 equivalents of t-butylchlorodiphenylsilane (TBDPSCl) in the presence of imidazole and 4-(dimethylamino)pyridine (DMAP) in N,N-dimethylformamide (DMF) affords monosilyl ether 11, which is oxidized with stoichiometric N-methylmorpholine N-oxide (NMO) in the presence of a catalytic amount of tetra-n-propylammonium perruthenate (TPAP) to provide aldehyde 12. Dibromoolefination of 12 using $CBr_4$ and $PPh_3$ gives 13. Conversion of 13 to enynol 15 is accomplished in two steps: first, treatment of 13 with 1 equivalent of $Bu_3SnH$ in toluene in the presence of a catalytic amount of $Pd(PPh_3)_4$ to afford the corresponding cis-vinyl bromide, followed by addition of CuI, $HNEt_2$, and chiral enantiopure propargyl alcohol 14 [for the preparation of 14, see: Midland et. al., Tetrahedron, 40:1371 (1984), which by this reference is incorporated herein]. Reduction of 15 with $Na[H_2Al(OCH_2CH_2OCH_3)_2]$ affords diene 16, which is treated with 3,4-dihydro-2H-pyran (DHP) and a catalytic amount of p-toluenesulfonic acid monohydrate (TsOH) to give ether 17. Desilylation of 17 with tetra-n-butylammonium fluoride (TBAF) yields alcohol 18, which is oxidized with TPAP/NMO to provide aldehyde 19. Condensation of 19 with $Ph_3P(CH_2)_4CO_2H$ Br in the presence of $KOBu^t$, followed by treatment of the resultant eneacid with pyridinium p-toluenesulfonate (PPTS) in warm methanol, affords 1.

EXAMPLE 2

Preparation of 2α and 2β

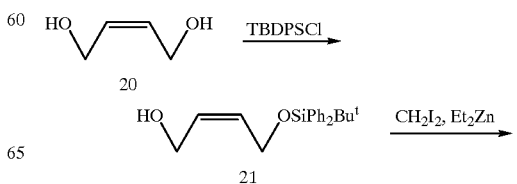

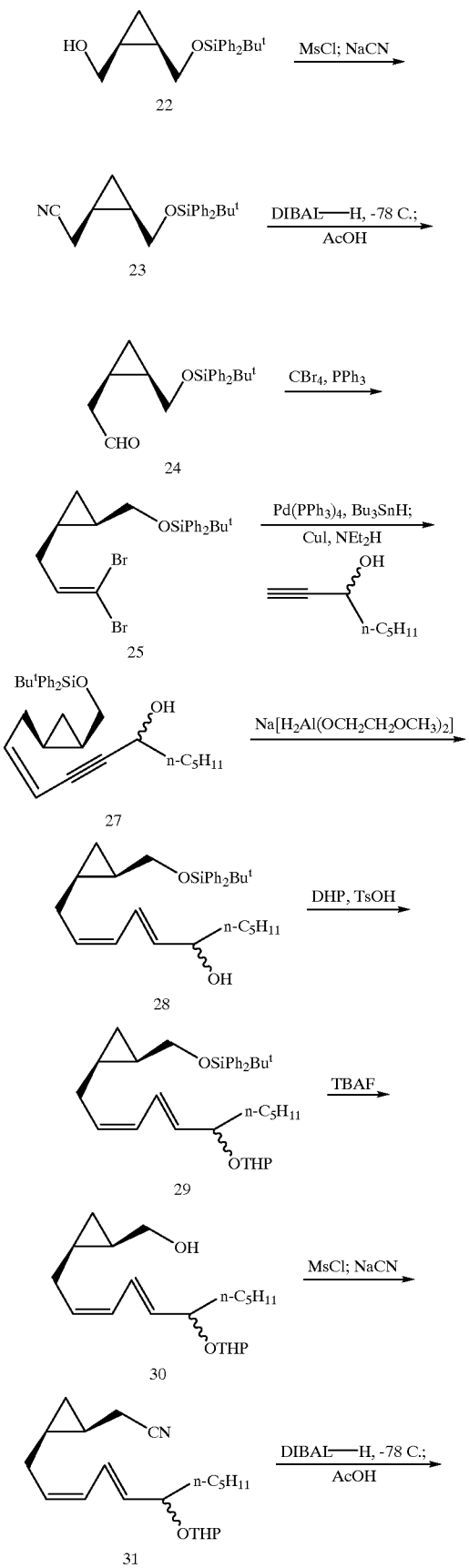
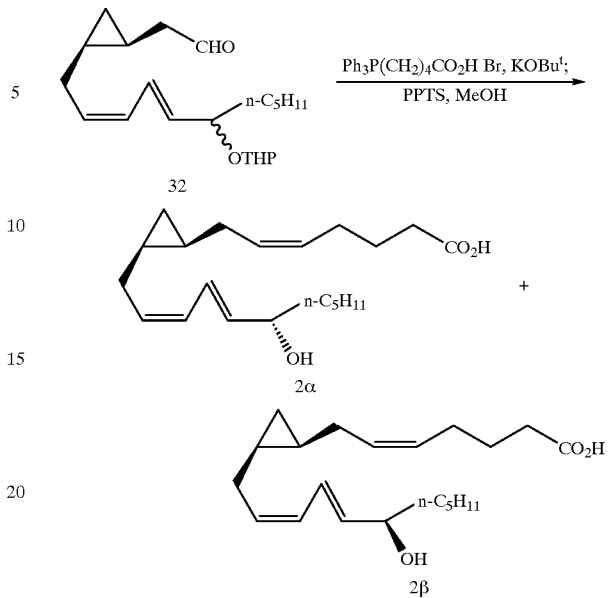

Compounds 2α and 2β

Monosilylation of (2Z)-2-buten-1,4-diol (20) with TBDP-SCl provides silyl ether 21, which is reacted with diiodomethane and diethylzinc to afford cyclopropane 22. Sequential reaction with mesyl chloride and NaCN provides nitrile 23. 23 is reduced with diisobutylaluminum hydride (DIBAL-H) at low temperature, and the intermediate imine is hydrolyzed with aqueous acetic acid to afford aldehyde 24. Condensation of 24 with $CBr_4$ and $PPh_3$ gives dibromoolefin 25. Monoreduction of 25 using stoichiometric $Bu_3SnH$ and catalytic $Pd(PPh_3)_4$ affords an intermediate Z-vinyl bromide, which in the same pot is reacted 1-octyn-3-ol (commercially available from Aldrich Chemical Co., Milwaukee, Wis.) in the presence of CuI and diethylamine to provide enyne 27. Reduction of 27 with sodium bis(2-methoxyethyoxy)aluminum hydride yields Z, E-dienyl alcohol 28, which is converted THP ether 29 using DHP and TsOH. Desilylation of 29 with TBAF affords alcohol 30, which is extended to cyanide 31 by sequential treatment with mesyl chloride and NaCN. Conversion to aldehyde 32 effected by reduction with DIBAL-H at −78° C., followed by hydrolysis of the resulting metalloenamine with aqueous acetic acid at 0° C. Wittig condensation with $Ph_3P(CH_2)_4 CO_2H$ Br in the presence of $KOBu^t$, followed by deprotection of the resultant eneacid with PPTS in MeOH, yields 2α and 2β after separation of the two C-15 diastereomers using silica gel chromatography.

EXAMPLE 3

Synthesis of 3α and 3β

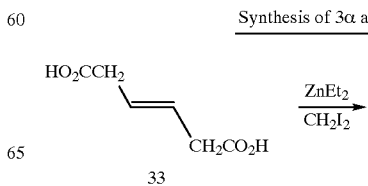

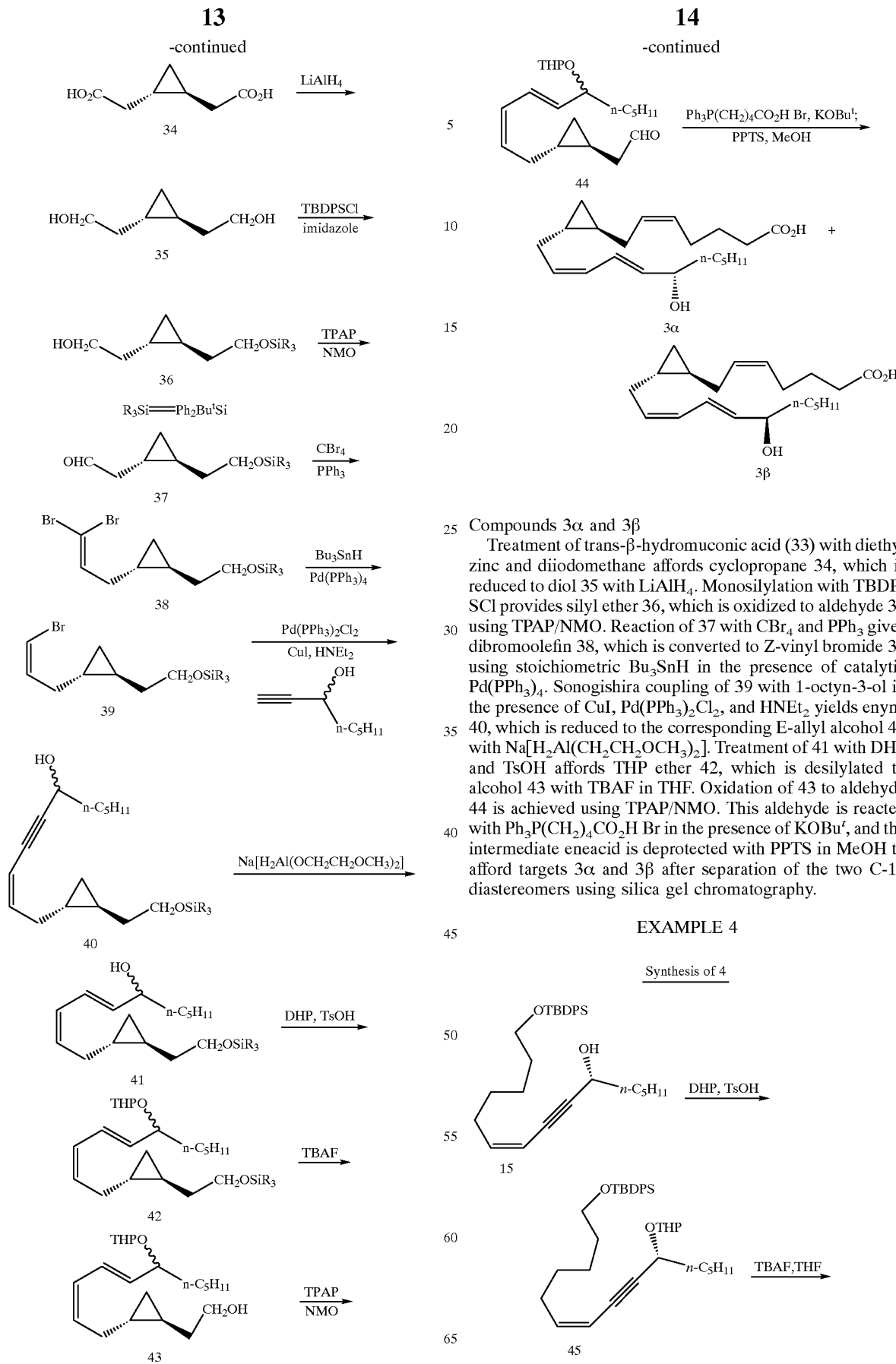

Compounds 3α and 3β

Treatment of trans-β-hydromuconic acid (33) with diethyl zinc and diiodomethane affords cyclopropane 34, which is reduced to diol 35 with LiAlH$_4$. Monosilylation with TBDPSCl provides silyl ether 36, which is oxidized to aldehyde 37 using TPAP/NMO. Reaction of 37 with CBr$_4$ and PPh$_3$ gives dibromoolefin 38, which is converted to Z-vinyl bromide 39 using stoichiometric Bu$_3$SnH in the presence of catalytic Pd(PPh$_3$)$_4$. Sonogishira coupling of 39 with 1-octyn-3-ol in the presence of CuI, Pd(PPh$_3$)$_2$Cl$_2$, and HNEt$_2$ yields enyne 40, which is reduced to the corresponding E-allyl alcohol 41 with Na[H$_2$Al(CH$_2$CH$_2$OCH$_3$)$_2$]. Treatment of 41 with DHP and TsOH affords THP ether 42, which is desilylated to alcohol 43 with TBAF in THF. Oxidation of 43 to aldehyde 44 is achieved using TPAP/NMO. This aldehyde is reacted with Ph$_3$P(CH$_2$)$_4$CO$_2$H Br in the presence of KOBu$^t$, and the intermediate eneacid is deprotected with PPTS in MeOH to afford targets 3α and 3β after separation of the two C-15 diastereomers using silica gel chromatography.

EXAMPLE 4

Synthesis of 4

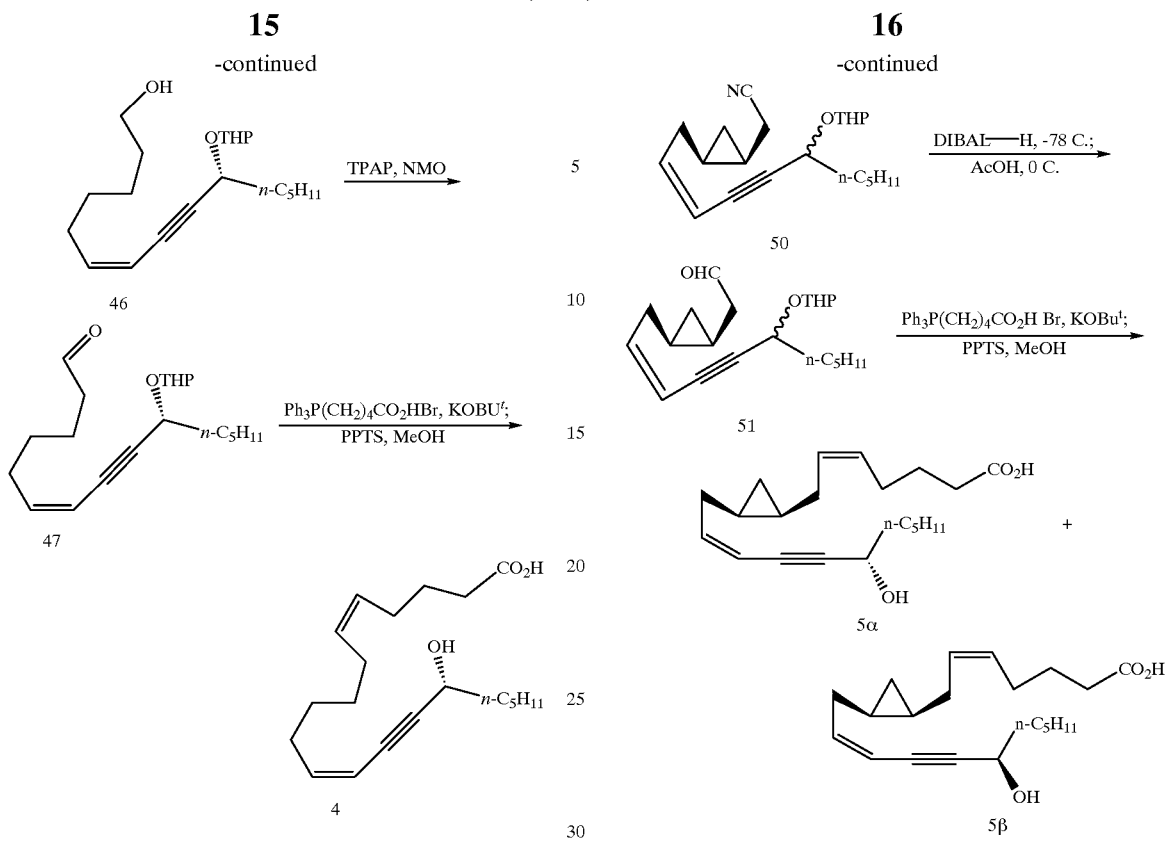

Compound 4

Alcohol 15 is protected as its THP ether 45 by treatment with DHP and TsOH. Desilylation of 45 with TBAF in THF provides alcohol 46, which is oxidized to aldehyde 47 with TPAP and NMO. Wittig reaction of 47 with $Ph_3P(CH_2)_4CO_2H\,Br$ in the presence of $KOBu^t$ affords an intermediate eneacid, which is deprotected to 4 using PPTS in MeOH.

EXAMPLE 5

Preparation of 5α and 5β

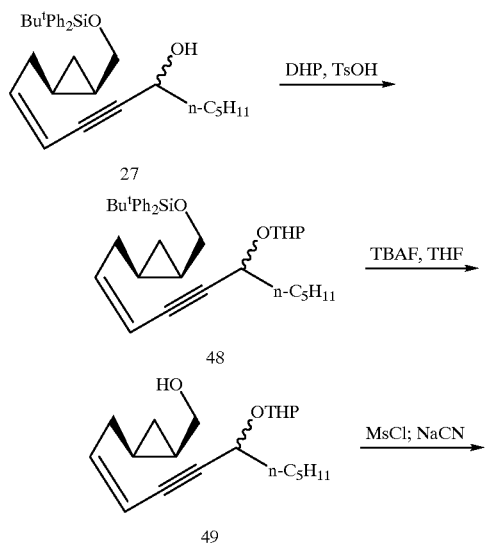

Compounds 5α and 5β

Treatment of enynol 27 with DHP and TsOH affords THP ether 48, which is desilylated using TBAF in THF to afford alcohol 49. Sequential treatment of 49 with mesyl chloride and then NaCN provides nitrile 50, which is reduced to aldehyde 51 by reaction with DIBAL-H at −78° C. and acetic acid at 0° C. Wittig condensation of 51 with $Ph_3P(CH_2)_4CO_2H\,Br$ in the presence of $KOBu^t$, followed by treatment of the intemediate eneacid with PPTS in MeOH, gives 5α and 5β after separation of the two C-15 diastereomers using silica gel chromatography.

EXAMPLE 6

Synthesis of 6

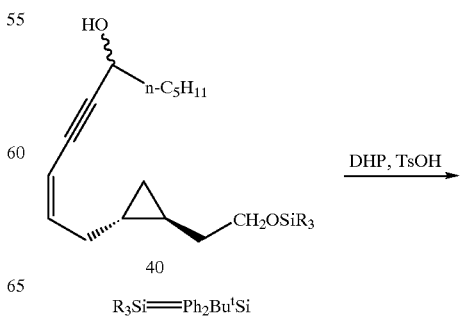

EXAMPLE 7

Synthesis of 7

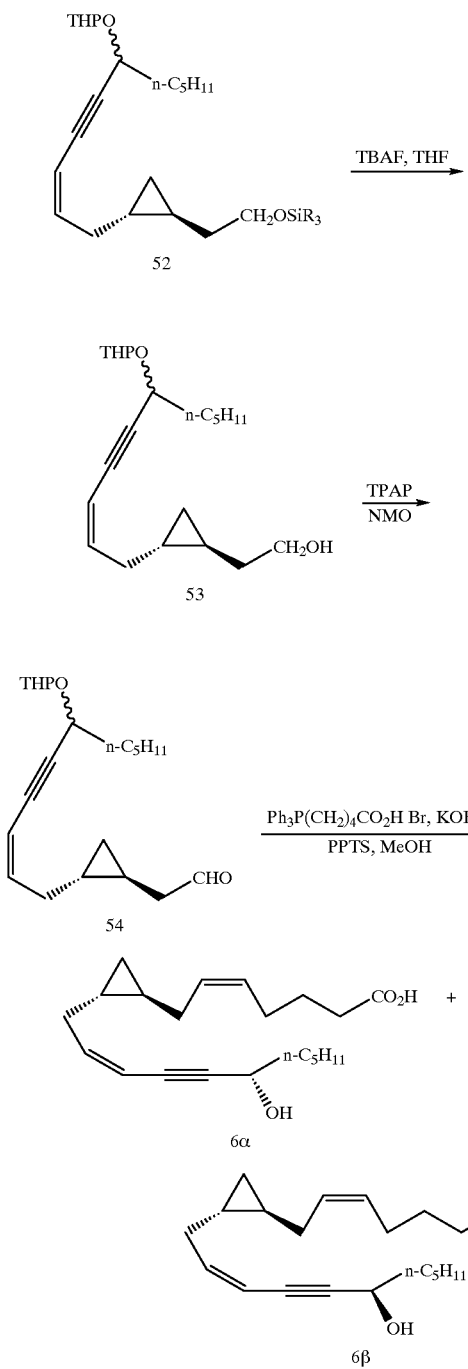

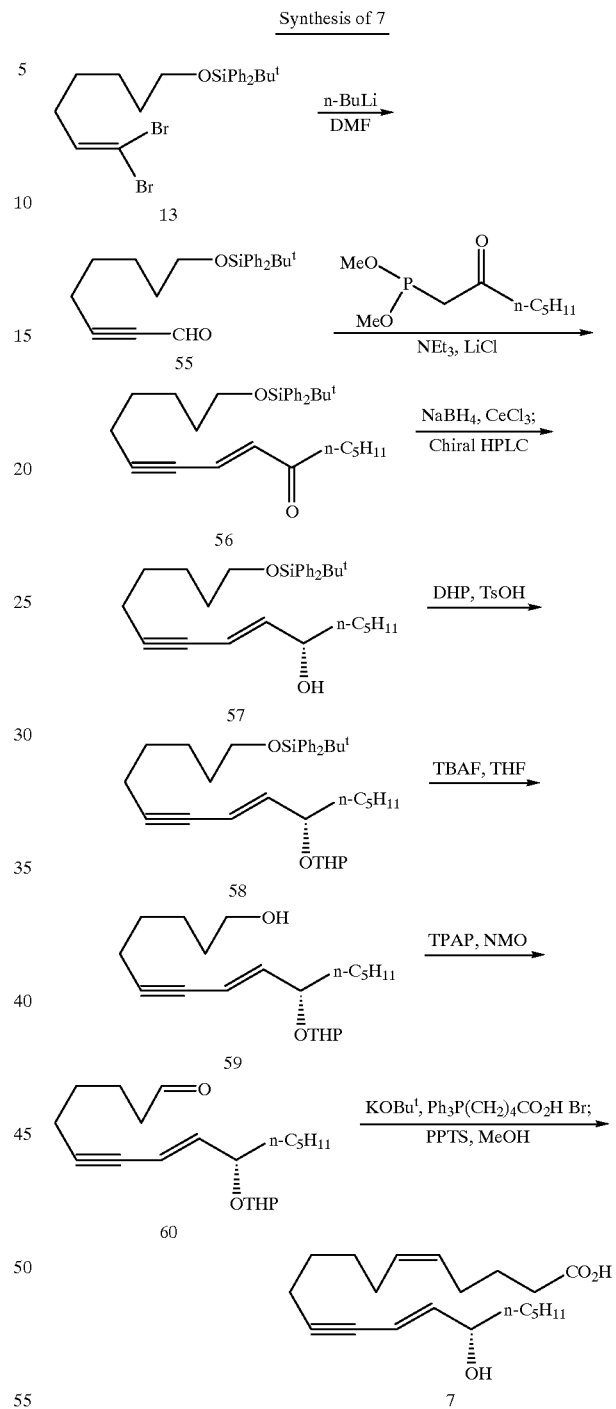

Compounds 6α and 6β

Reaction of enynol 40 with DHP and TsOH affords THP ether 52, which is desilylated using TBAF in THF to afford alcohol 53. Oxidation of 53 using TPAP and NMO provides aldehyde 54, which undergoes Wittig condensation with $Ph_3P(CH_2)_4CO_2H\ Br/KOBu^t$ and deprotection with PPTS in MeOH to give compounds 6α and 6β after separation of the two C-15 diastereomers using silica gel chromatography.

Compound 7

Treatment of dibromoolefin 13 with n-BuLi and N,N-dimethylformamide affords ynal 55, which is condensed with dimethyl (2-oxoheptyl)phosphonate in the presence of $NEt_3$ and LiCl to provide enone 56. 56 is reduced to 15S-alcohol 57 by treatment with $NaBH_4$ and $CeCl_3$, followed by separation of the resulting racemic mixture using HPLC with a chiral stationary phase. Treatment of 57 with DHP and TsOH gives THP ether 58, which is desilylated with TBAF in THF to yield alcohol 59. Oxidation of 59 with TPAP and NMO affords aldehyde 60. 60 is treated with Ph$_3$P(CH$_2$)$_4$CO$_2$H Br in the presence of KOBu$^t$, followed by PPTS in MeOH, to give 7.

EXAMPLE 8

Preparation of 8α and 8β

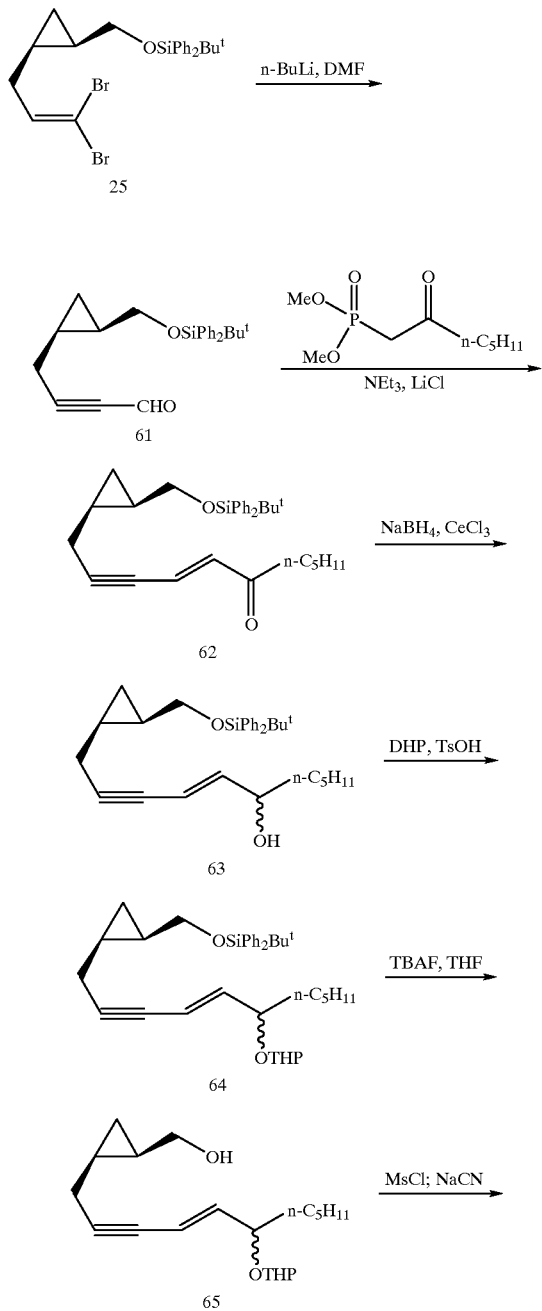

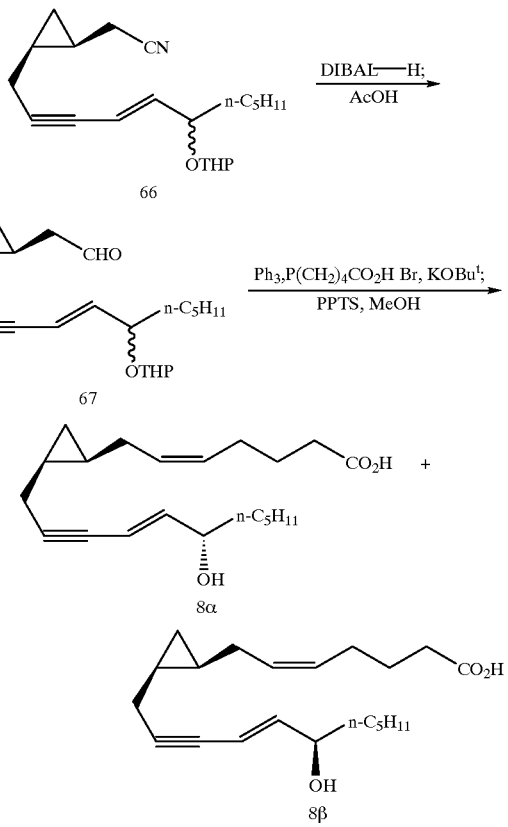

Compounds 8α and 8β

Treatment of dibromoolefin 25 with n-BuLi and N,N-dimethylformamide affords ynal 61, which is condensed with dimethyl (2-oxoheptyl)phosphonate in the presence of NEt$_3$ and LiCl to provide enone 62. 62 is reduced to 15R,S-alcohol 63 by treatment with NaBH$_4$ and CeCl$_3$. Treatment of 63 with DHP and TsOH gives THP ether 64, which is desilylated with TBAF in THF to yield alcohol 65. Sequential treatment of 65 with mesyl chloride and then NaCN affords nitrile 66. 66 is converted to aldehyde 67 by reduction with DIBAL-H at −78° C., followed by hydrolysis acetic acid at 0° C. 67 is treated with Ph$_3$P(CH$_2$)$_4$CO$_2$H Br in the presence of KOBu$^t$, followed by PPTS in MeOH, to give targets 8α and 8β after separation of the two C-15 diastereomers using silica gel chromatography.

EXAMPLE 9

Preparation of 9α and 9β

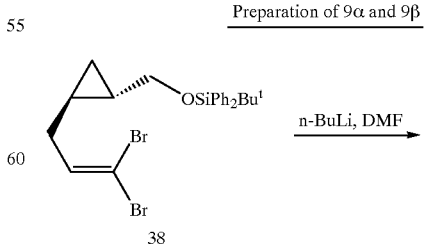

-continued

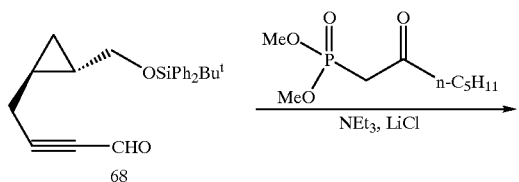
68

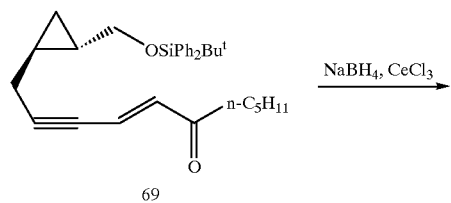
69

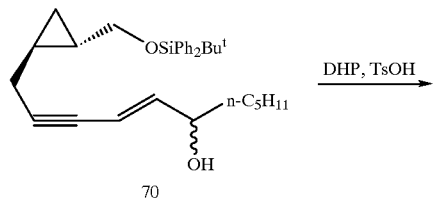
70

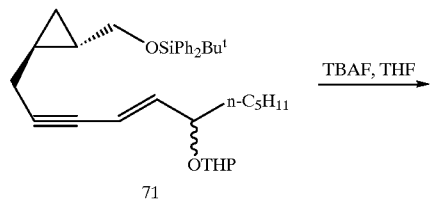
71

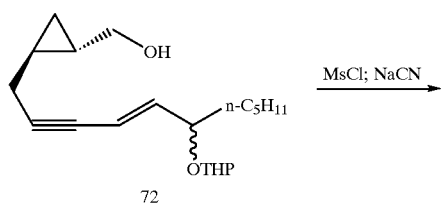
72

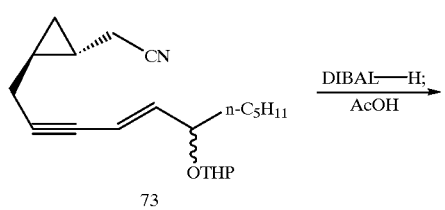
73

-continued

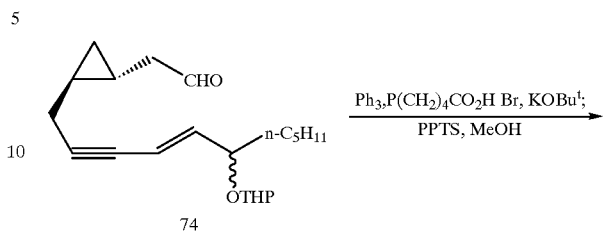
74

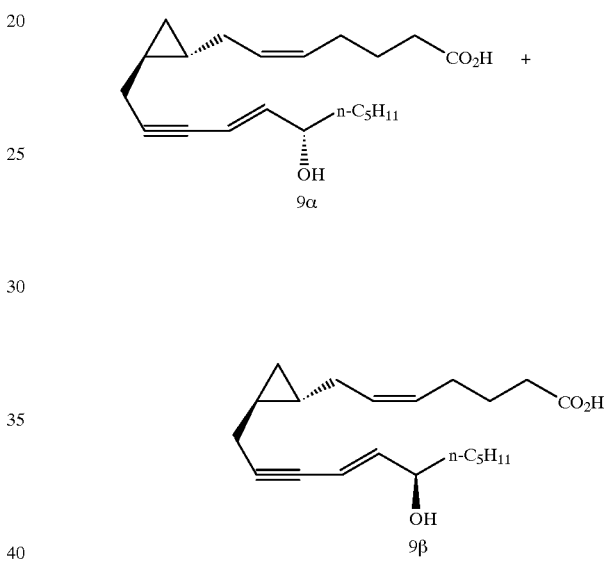

Compounds 9α and 9β

Treatment of dibromoolefin 38 with n-BuLi and N,N-dimethylformamide affords ynal 68, which is condensed with dimethyl (2-oxoheptyl)phosphonate in the presence of $NEt_3$ and LiCl to provide enone 69. 69 is reduced to 15R,S-alcohol 70 by treatment with $NaBH_4$ and $CeCl_3$. Treatment of 70 with DHP and TsOH gives THP ether 71, which is desilylated with TBAF in THF to yield alcohol 72. Sequential treatment of 72 with mesyl chloride and then NaCN affords nitrile 73. 73 is converted to aldehyde 74 by reduction with DIBAL-H at −78° C., followed by hydrolysis acetic acid at 0° C. 74 is treated with $Ph_3P(CH_2)_4CO_2H$ Br in the presence of $KOBu^t$, followed by PPTS in MeOH, to give compounds 9α and 9β after separation of the two C-15 diastereomers using silica gel chromatography.

EXAMPLE 10

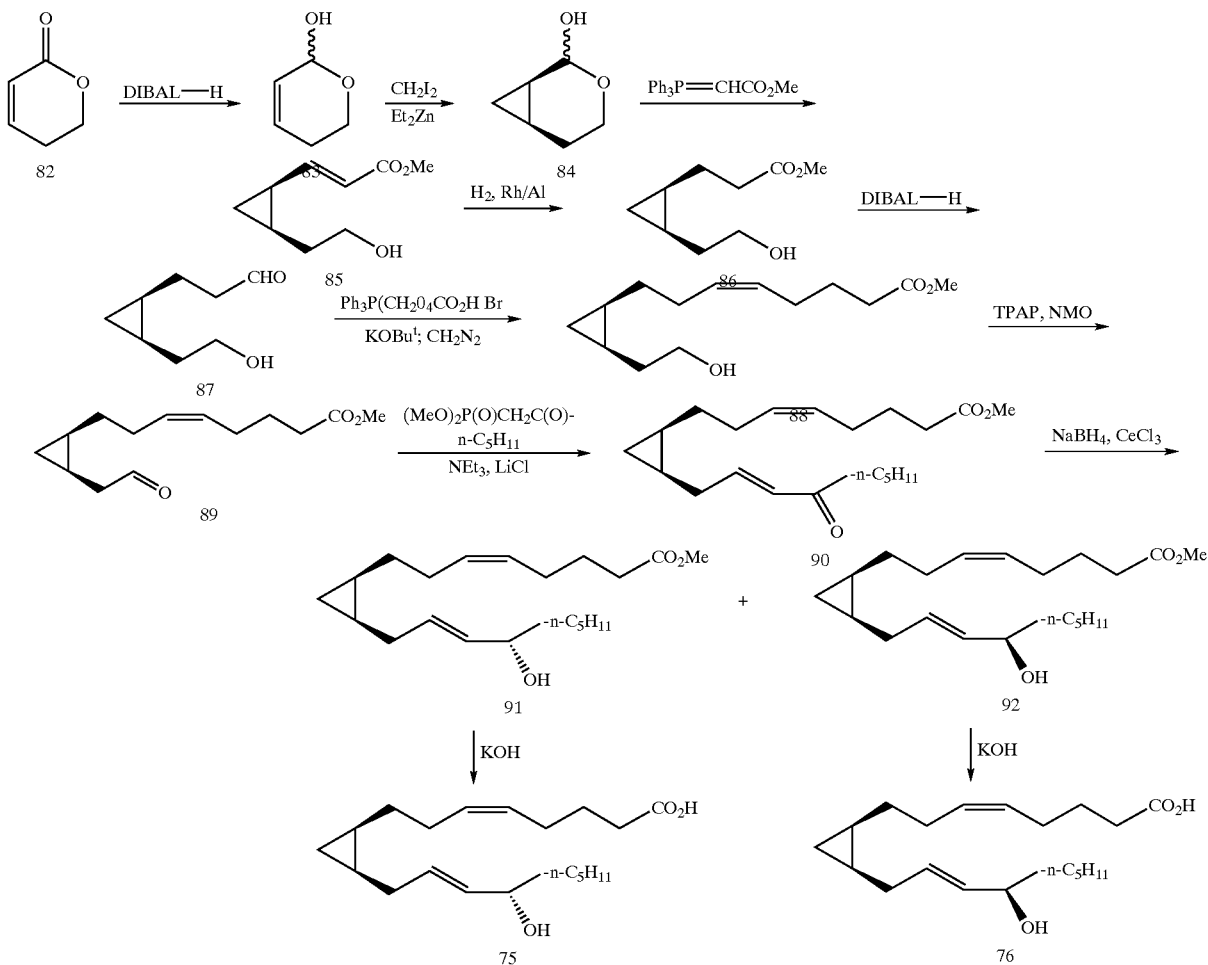

Compounds 75 and 76

Reduction of commercially available dihydropyranone 82 with diisobutylaluminum hydride (DIBAL-H) affords lactol 83, which is cyclopropanated with $CH_2I_2/Et_2Zn$ to provide 84. 84 is condensed with $Ph_3P=CHCO_2CH_3$ to yield enoate 85, which is reduced under 1 atmosphere of hydrogen using Rhodium on Alumina catalyst to give 86. 86 is converted to aldehyde 87 by reduction with DIBAL-H. Condensation of 87 with $Ph_3P(CH_2)_4CO_2H$ Br in the presence of potassium t-butoxide (KOBu$^t$), followed by treatment of the intermediate acid with diazomethane, provides olefin 88. Oxidation of 88 using catalytic tetra-n-propylammonium perruthenate (TPAP) and stoichiometric N-methylmorpholine N-oxide (NMO) gives aldehyde 89, which is condensed with dimethyl (2-oxoheptyl)phosphonate in the presence of $NEt_3$ and LiCl to provide enone 90. Treatment of 90 with $NaBH_4$ in the presence of $CeCl_3$ affords a mixture of two stereoisomeric alcohols, 91 and 92, which are separated using silica gel chromatography. Treatment of the thus separated samples of 91 and 92 with KOH in MeOH/water affords the corresponding acids 75 and 76.

EXAMPLE 11

Preparation of 77 and 78

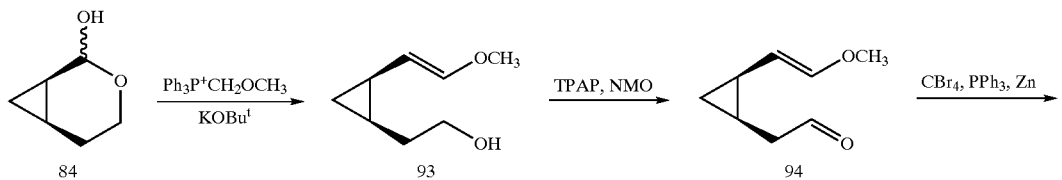

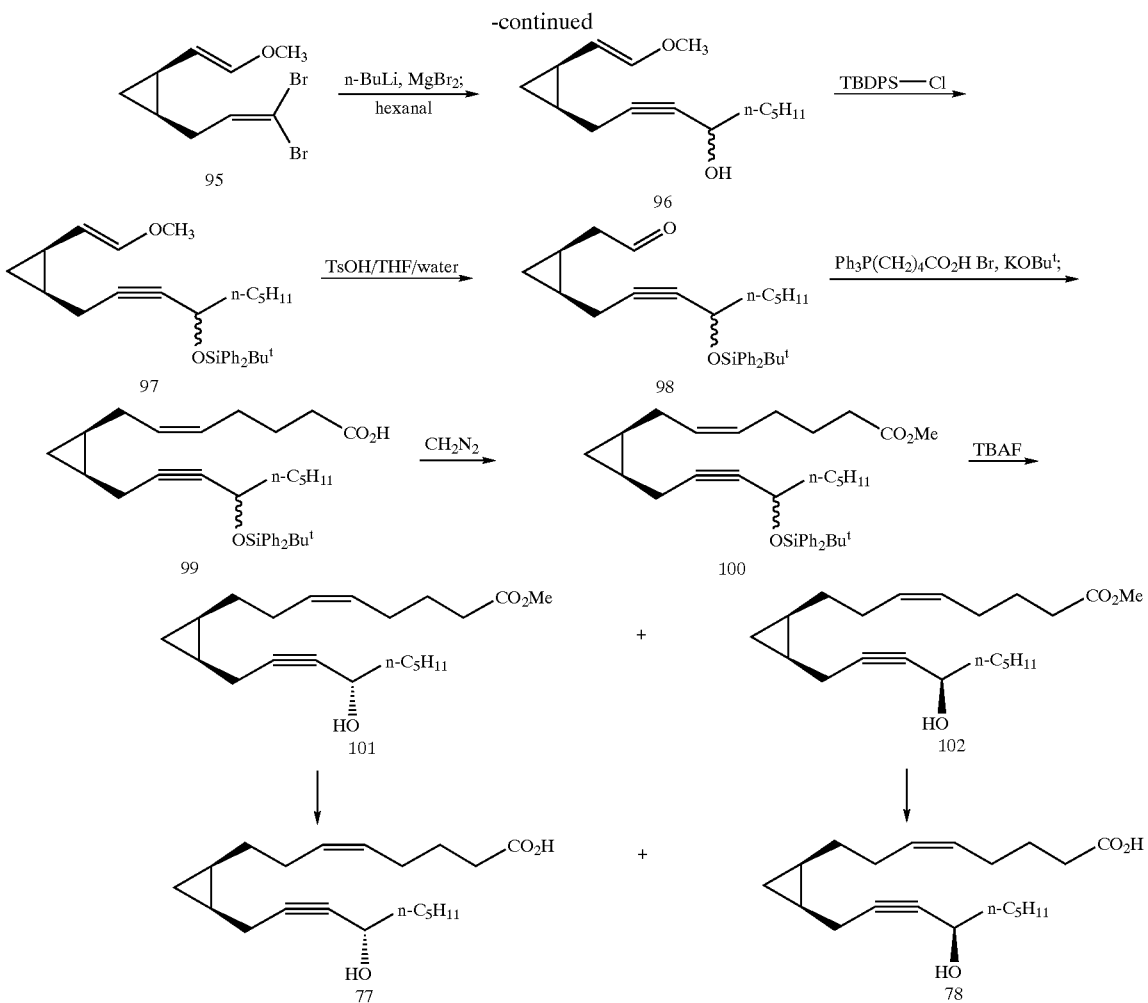

Compounds 77 and 78

Reaction of lactol 84 with Ph$_3$P$^+$CH$_2$OCH$_3$Cl$^-$ in the presence of KOBu$^t$ affords enol ether 93, which is oxidized using TPAP/NMO to afford aldehyde 94. Corey-Fuchs reaction of 94 with CBr$_4$, PPh$_3$, and Zn provides dibromoolefin 95, sequential treatment of which with n-BuLi, MgBr$_2$, and hexanal gives propargyl alcohol 96. Treatment of 96 with t-butylchlorodiphenylsilane (TBDPSCl) and imidazole in the presence of catalytic 4-(dimethylamino)pyridine (DMAP) yields silyl ether 97, which is treated with TsOH in hot THF/water to provide alcohol 98. Wittig condensation of 98 with Ph$_3$P(CH$_2$)$_4$CO$_2$H Br in the presence of KOBu$^t$ affords acid 99, which is esterified using diazomethane to provide enyne 100. Treatment of 100 with tetra-n-butylammonium fluoride (TBAF) in THF, followed by chromatographic purification, gives the individual diastereomers 100 and 101. These are converted to their respective free acids 77 and 78 by treatment with KOH in MeOH/water.

EXAMPLE 12

Preparation of 79 and 80

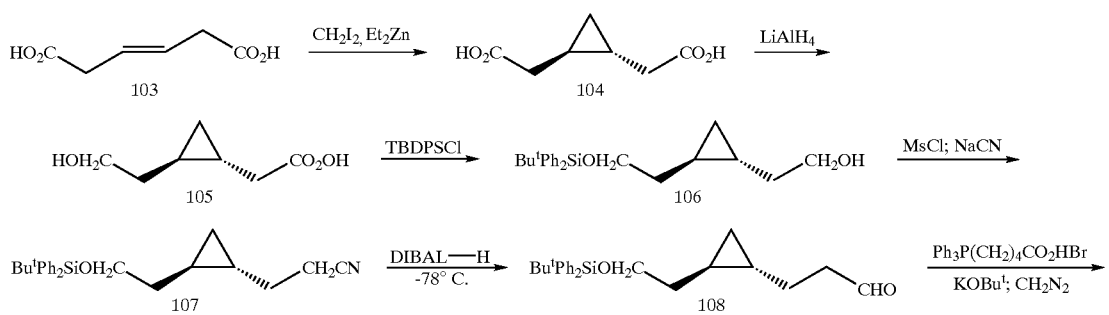

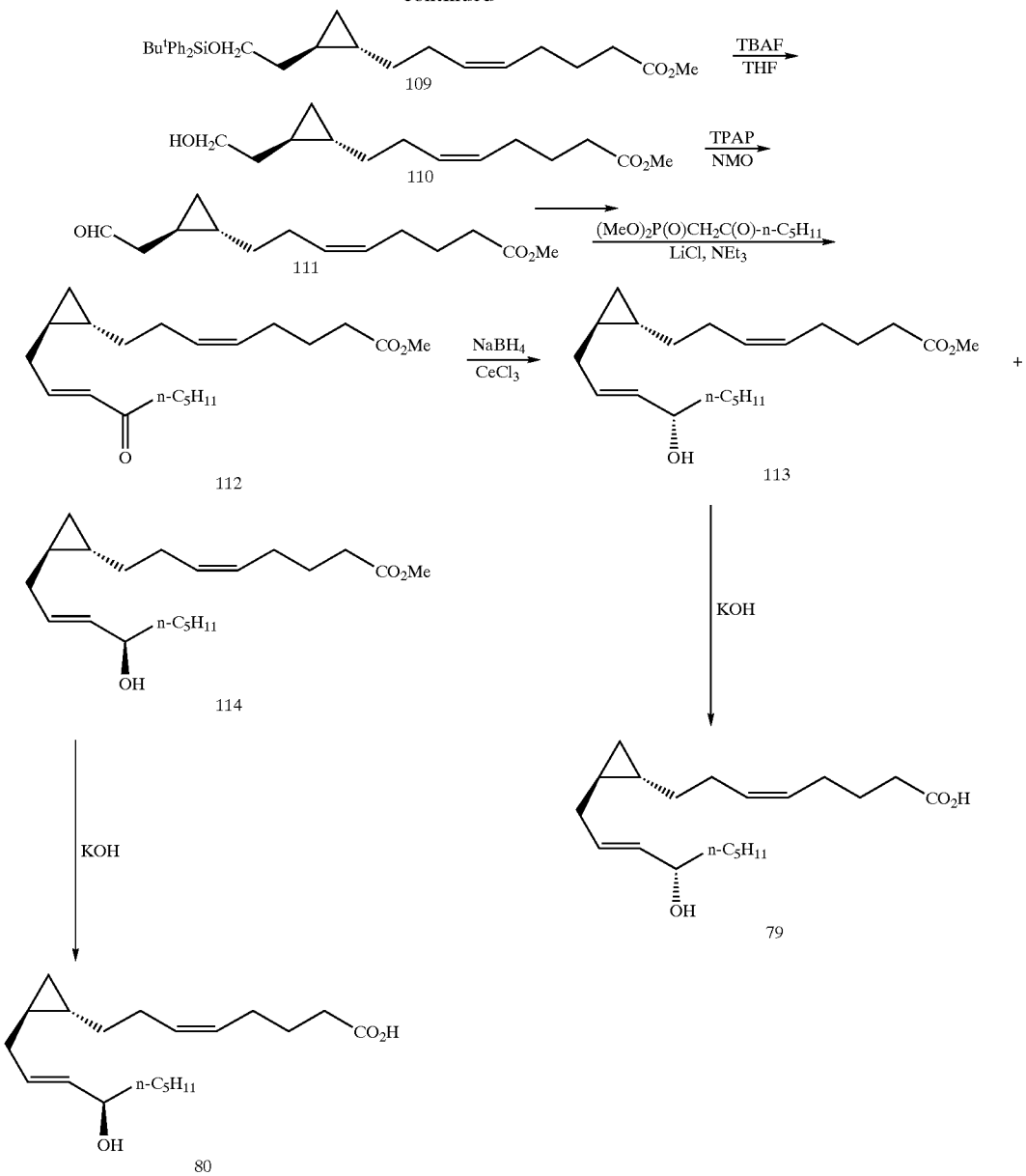

Compounds 79 and 80

Treatment of trans-β-hydromuconic acid (103) with $CH_2I_2/Et_2Zn$ affords cyclopropane 104, which is reduced to diol 105 with $LiAlH_4$. 105 is monosilylated with TBDPSCl in the presence of imidazole and DMAP provide silyl ether 106, which is treated sequentially with MsCl in $CH_2Cl_2$ and then NaCN in DMSO to give nitrile 107. 107 is converted to aldehyde 108 by treatment with DIBAL-H at −78° C. followed by aqueous acetic acid at 0° C. 108 is condensed with $Ph_3P(CH_2)_4CO_2H$ Br in the presence of $KOBu^t$, followed by esterification of the intermediate acid with diazomethane, to afford olefin 109. 109 is deprotected using TBAF in THF to give alcohol 119 which is oxidized using TPAP/NMO to yield aldehyde 111. 111 is condensed with dimethyl (2-oxoheptyl)phosphonate in the presence of LiCl and $NEt_3$ to give enone 112, which is reduced using $NaBH_4/CeCl_3$ to provide the α and β allyl alcohol diastereomers 113 and 114 after chromatographic purification. Saponification of each of these esters using KOH in aqueous methanol affords the acids 79 and 80 respectively.

EXAMPLE 13

Preparation of 81 and 82

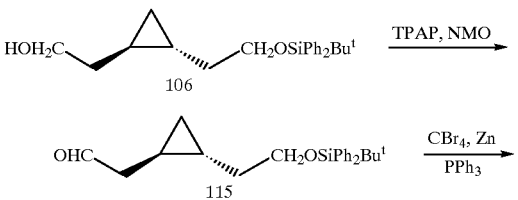

-continued

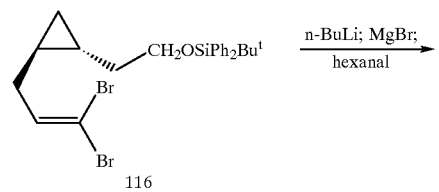

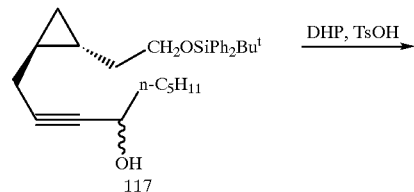

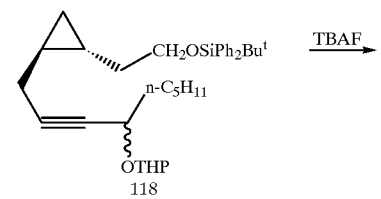

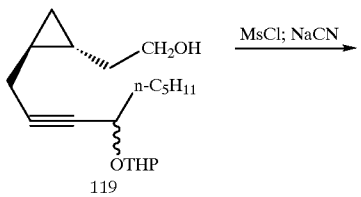

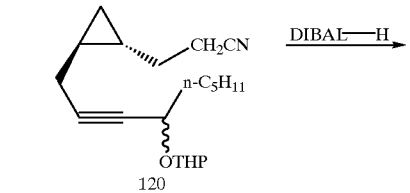

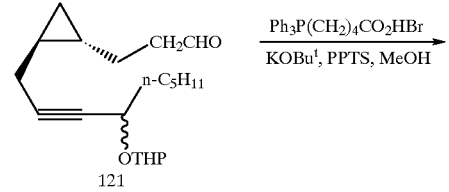

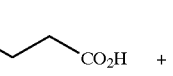

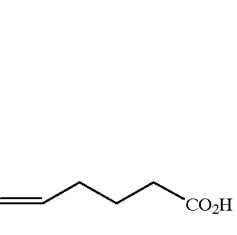

Compounds 81 and 82

Alcohol 106 is oxidized using TPAP/NMO to give aldehyde 115, which is condensed with $CBr_4$ in the presence of $PPh_3$ and Zn to afford dibromoolefin 116. Treatment of 116 successively with n-BuLi, then $MgBr_2$, and finally hexanal affords ynol 117. 117 is protected as its THP ether by treatment with DHP and TsOH to give 118. Desilylation of 118 with TBAF in THF affords alcohol 119, which is treated sequentially with MsCl in $CH_2Cl_2$ and then NaCN in DMSO to yield nitrile 120. Reduction of 120 with DIBAL-H at −78° C., followed by hydrolysis with aqueous acetic acid at 0° C., gives aldehyde 121. Condensation of 121 with $Ph_3P(CH_2)_4CO_2H$ Br in the presence of $KOBu^t$, followed by treatment of the intermediate THP ether acid with pyridinium p-toluenesulfonate (PPTS) in warm methanol, affords the individual α and β propargyl alcohol diastereomeric acids 81 and 82 after chromatographic purification.

EXAMPLE 14

Synthesis of 122 and 123

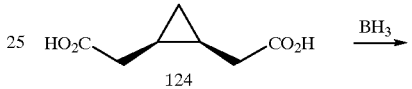

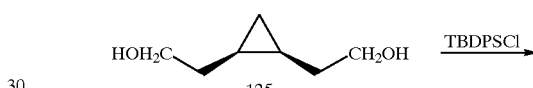

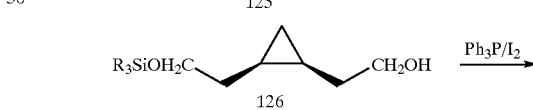

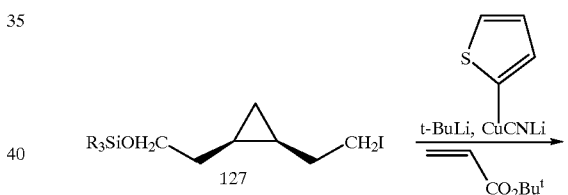

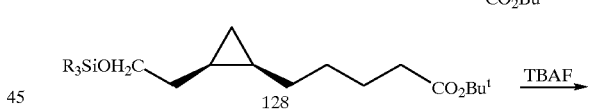

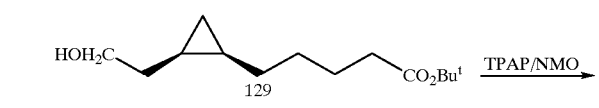

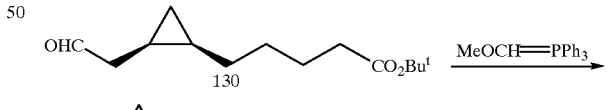

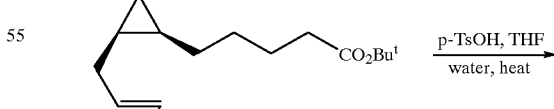

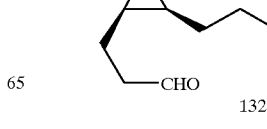

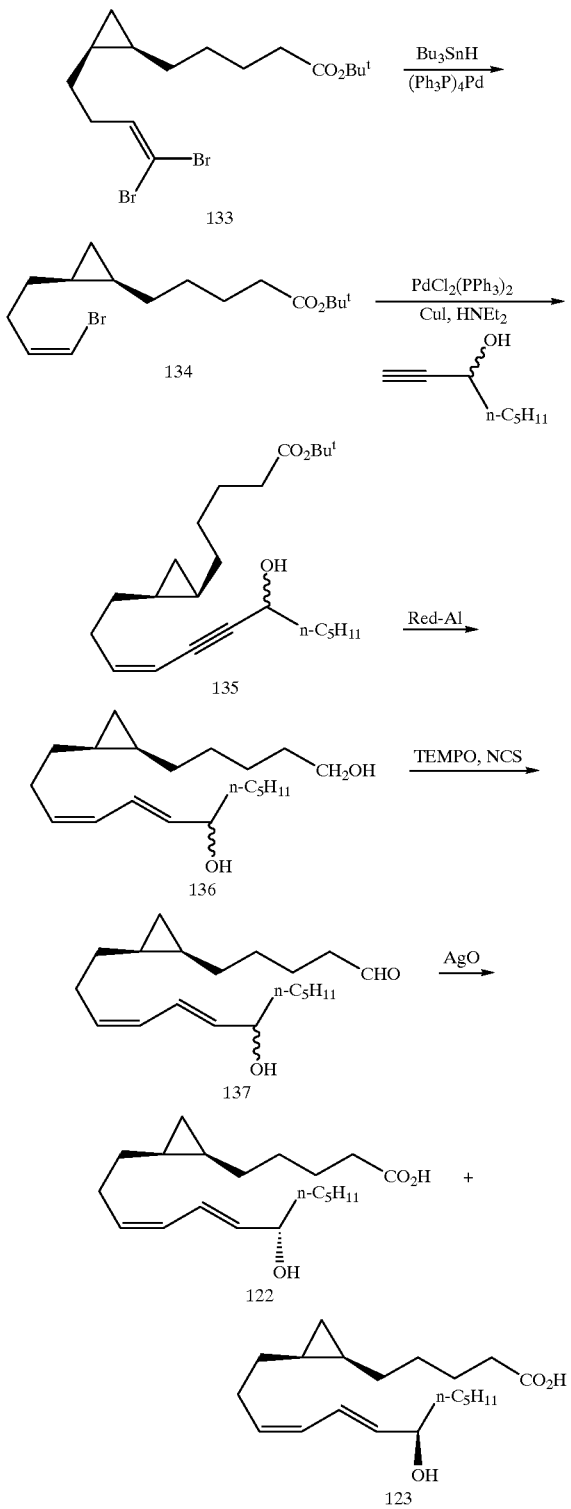

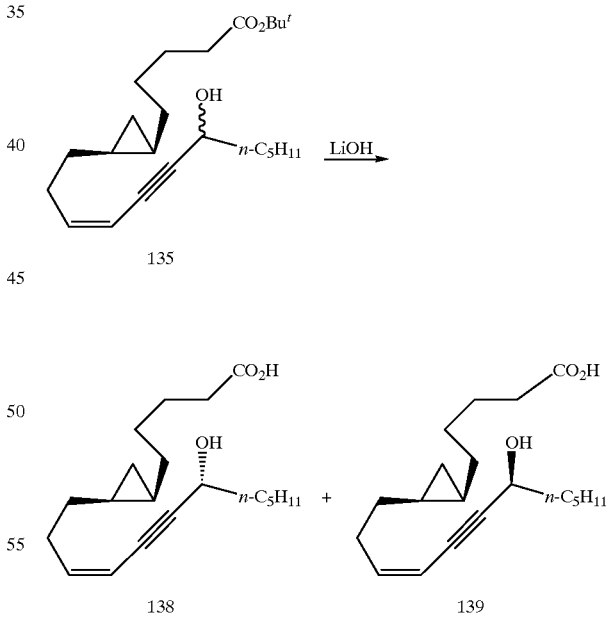

imidazole affords iodide 127. 127 is treated sequentially with with t-butyllithium at −78° C., lithium (2-thienyl) cyanocuprate, and 1-butyl acrylate to afford the Michael adduct 128 after quenching with aqueous acid. 128 is desilylated to alcohol 129 using tetra-n-butylammonium fluoride (TBAF) in THF. Oxidation of 129 with catalytic tetra-n-propylammonium perrruthernate (TPAP) and stoichiometric N-methylmorpholine-N-oxide (NMO) provides aldehyde 130, which is converted to enol ether 131 by Wittig reaction with MeOCH=PPh₃. Hydrolysis of 131 using catalytic p-toluenesulfonic acid monohydrate (TsOH) in THF/water with heating affords homologated aldehyde 132, which is converted to dibromoolefin 133 by condensation with $CBr_4$ in the presence of $PPh_3$. Selective monoreduction of 133 with $Bu_3SnH$ in the presence of catalytic $Pd(PPh_3)_4$ gives Z-bromoalkene 134, which upon treatment with 1-octyn-3-ol, CuI, and catalytic $PdCl_2(PPh_3)_2$ in $HNEt_2$ yields enynol 135. 135 is reduced with $Na[H_2Al(OCH_2CH_2OCH_3)_2]$ (Red-Al®) in toluene to provide diene diol 136, which is selectively oxidized to hydroxyaldehyde 137 using catalytic 2,2,6,6-tetramethylpiperidinoxyl free radical (TEMPO) and stoichiometric N-chlorosuccinimide (NCS). Oxidation of 137 with silver (II) oxide, followed by chromatographic separation of the allyl alcohol diastereomers, affords the α isomer 122 and the β isomer 123.

EXAMPLE 15

Synthesis of 138 and 139

Compounds 138 and 139

Saponification of ester 135 with LiOH in methanol/water, followed by chromatographic separation of the propargyl alcohol diastereomers, affords targets 138 and 139.

Compounds 122 and 123

Reduction of diacid 124 (for the preparation of 13, see: Neset et. al., *Tetrahedron* 1997, 53,10459, which is incorporated herein by reference) with $BH_3$ affords diol 125, which is silylated with t-butyldiphenylsilyl chloride (TBDPSCl) in the presence of 4-(dimethylamino)pyridine (DMAP) and imidazole to afford silyl ether 126. Treatment of 126 with $I_2$ and $PPh_3$ in toluene in the presence of

EXAMPLE 16

Synthesis of 144 and 145

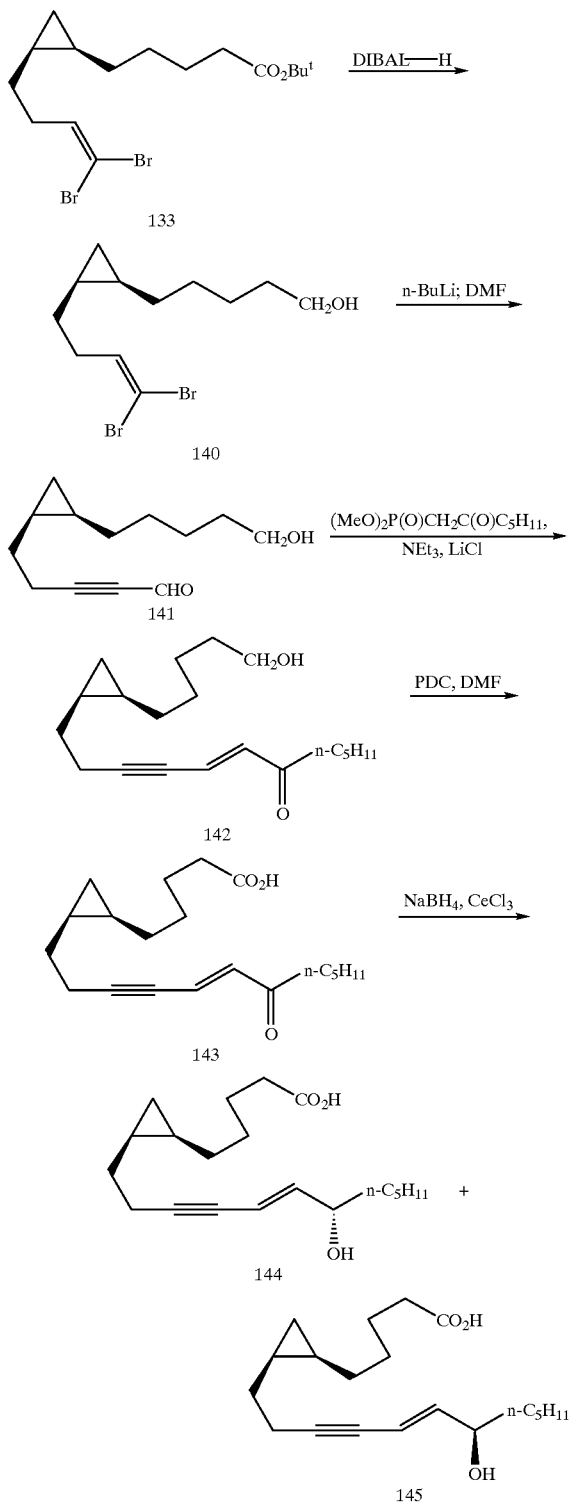

Compounds 144 and 145

Reduction of ester 133 with diisobutylaluminum hydride (DIBAL-H) affords alcohol 140, which is treated with three equivalents of n-butyllithium at −78° C. and then with N,N-dimethylformamide (DMF) to provide ynal 141. Horner-Emmons condensation of 141 with dimethyl (2-oxoheptyl)phosphonate in the presence of LiCl and $NEt_3$ gives ynenone 142, which is oxidized to acid 143 using pyridinium dichromate (PDC) in DMF. Reduction of 143 using $NaBH_4$ in the presence of $CeCl_3$, followed by chromatographic separation of the two allyl alcohol diastereomers, affords compounds 144 and 145.

EXAMPLE 17

Synthesis of 160 and 161

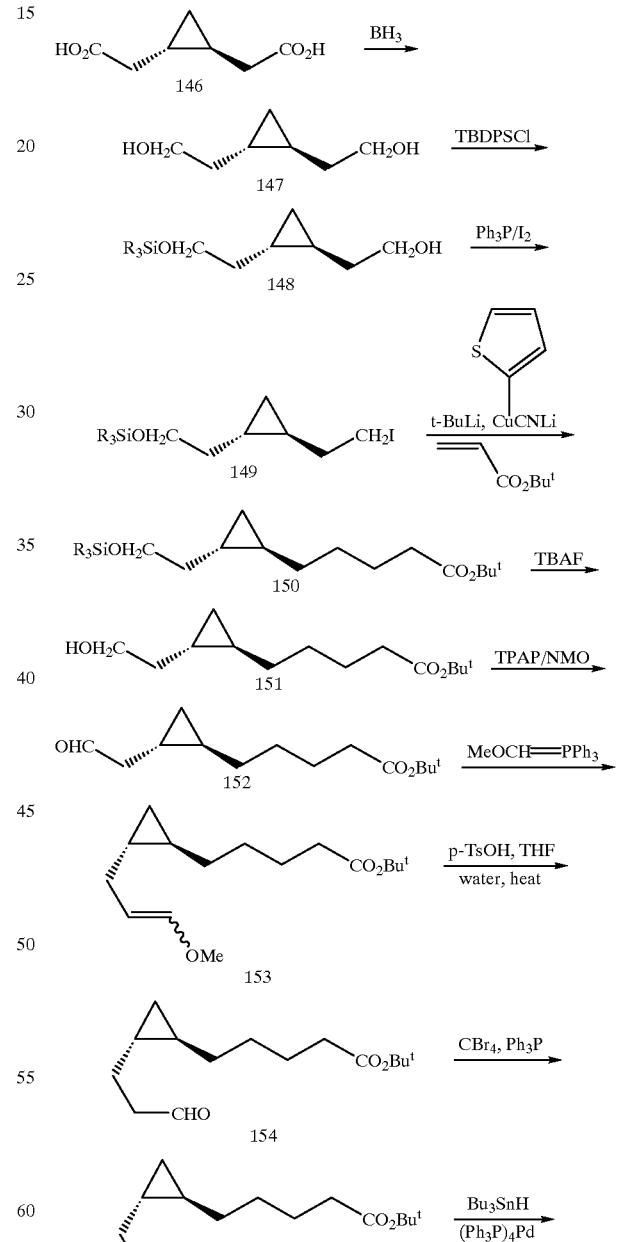

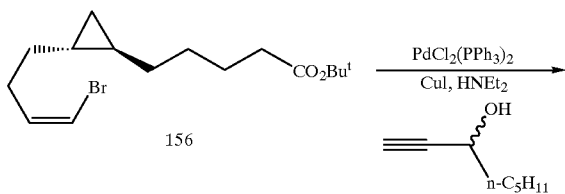

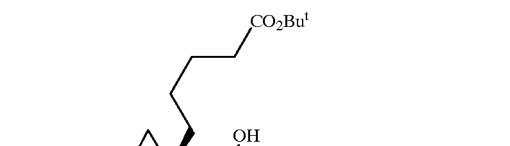

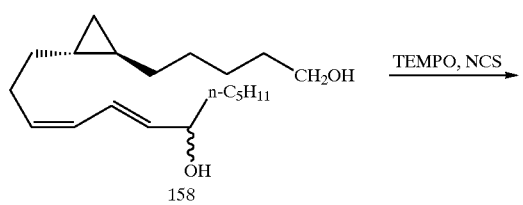

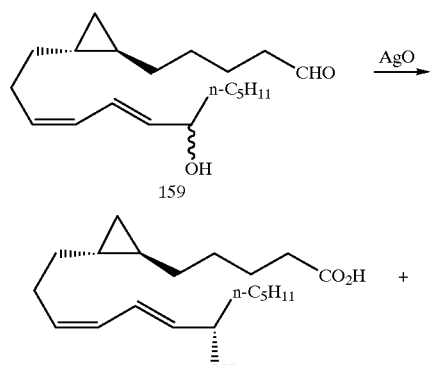

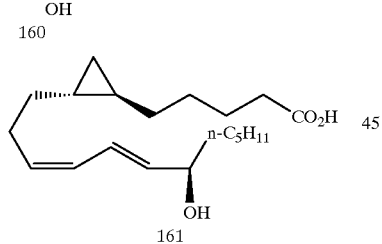

Compounds 160 and 161

Reduction of diacid 146 (Neset et. al., *Tetrahedron* 1997, 53, 10459) with BH₃•SMe₂ affords diol 147, which is silylated with TBDPSCl in the presence of DMAP and imidazole to afford silyl ether 148. Treatment of 148 with I₂ and PPh₃ in toluene in the presence of imidazole affords iodide 149. 149 is treated sequentially with with t-butyllithium at −78° C., then lithium (2-thienyl) cyanocuprate, then t-butyl acrylate to afford the Michael adduct 150 after quenching with aqueous acid. 150 is desilylated to alcohol 151 using TBAF in THF. Oxidation of 151 with catalytic TPAP and stoichiometric NMO provides aldehyde 152, which is converted to enol ether 153 by Wittig reaction with MeOCH=PPh₃. Hydrolysis of 153 using TsOH in THF/water with heating affords homologated aldehyde 154, which is converted to dibromoolefin 155 by condensation with CBr₄ in the presence of PPh₃. Selective monoreduction of 155 with Bu₃SnH in the presence of catalytic Pd(PPh₃)₄ gives Z-bromoalkene 156, which upon treatment with 1-octyn-3-ol, CuI, and catalytic PdCl₂(PPh₃)₂ in HNEt₂ yields enynol 157. 157 is reduced with Red-Al® in toluene to provide diene diol 158, which is selectively oxidized to hydroxyaldehyde 159 using TEMPO and stoichiometric NCS. Oxidation of 159 with silver (II) oxide, followed by chromatographic separation of the allyl alcohol diastereomers, affords the α isomer 160 and the β isomer 161.

EXAMPLE 18

Synthesis of 162 and 163

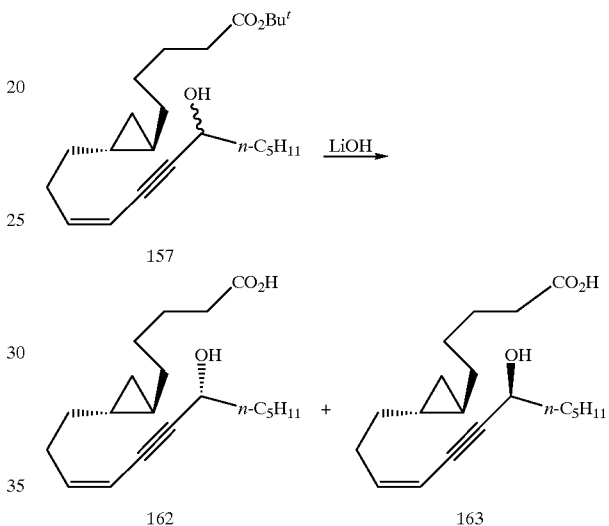

Compounds 162 and 163

Ester 157 is treated with KOH in MeOH/water followed by chromatographic separation of the propargyl alcohol diastereomers to afford targets 162 and 163.

EXAMPLE 19

Synthesis of 168 and 169

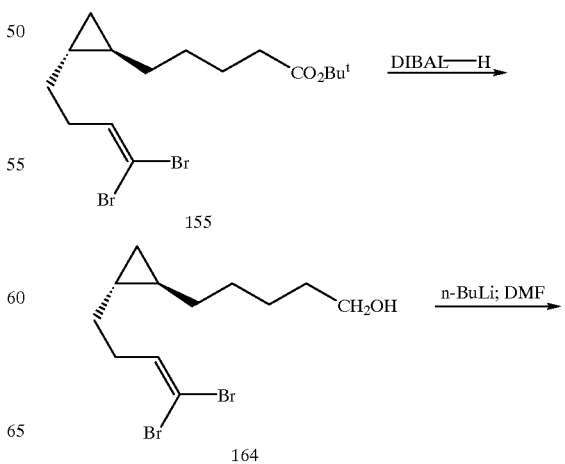

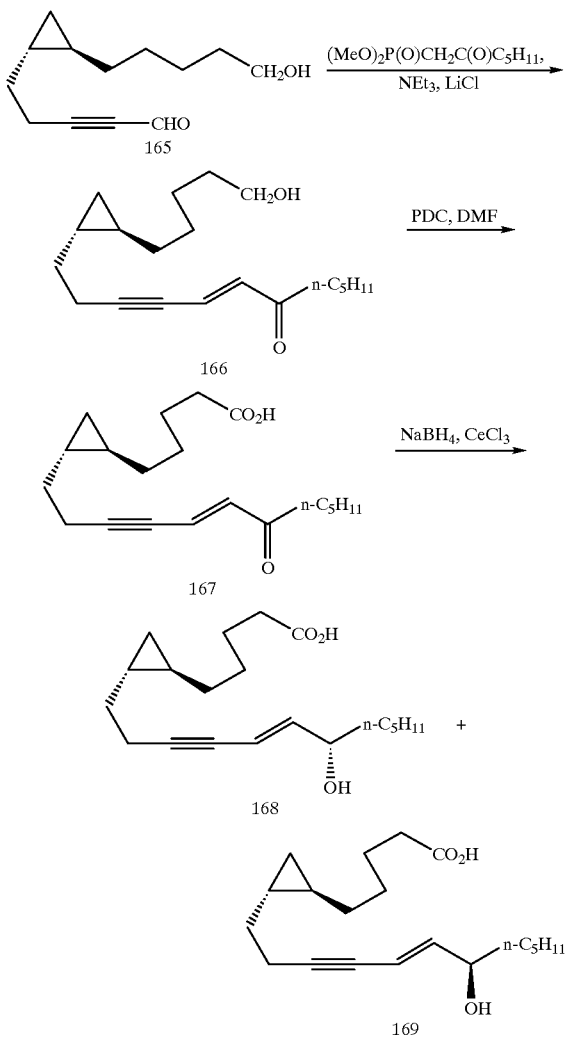

Compounds 168 and 169

Reduction of ester 155 with diisobutylaluminum hydride (DIBAL-H) affords alcohol 164, which is treated with three equivalents of n-butyllithium at −78° C. and then with N,N-dimethylformamide (DMF) to provide ynal 165. Homer-Emmons condensation of 165 with dimethyl (2-oxoheptyl)phosphonate in the presence of LiCl and $NEt_3$ gives ynenone 166, which is oxidized to acid 167 using pyridinium dichromate (PDC) in DMF. Reduction of 167 using $NaBH_4$ in the presence of $CeCl_3$, followed by chromatographic separation of the two allyl alcohol diastereomers, affords compounds 168 and 169.

The compounds of the present invention may be contained in various types of pharmaceutical compositions, in accordance with formulation techniques known to those skilled in the art. Preferably, these compounds will be formulated in solutions for topical ophthalmic administration.

The ophthalmic compositions of the present invention will include one or more compounds of the present invention in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the compounds of the present invention may also be readily incorporated into other types of compositions, such as suspensions, viscous or semi-viscous gels, or other types of solid or semi-solid compositions. Suspensions may be preferred for those compounds of the present invention which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the active ingredients from oxidation during storage. Examples of such antioxidants include vitamin E and analogs thereof, ascorbic acid and butylated hydroxytoluene (BHT).

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to increase mucin production in the eye and thus eliminate or improve dry eye conditions. As used herein, the term "pharmaceutically effective amount" refers to an amount which improves the dry eye condition in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any vehicle which, when formulated, is safe, and provides the appropriate delivery for the desired route of administration of an effective amount of at least one compound of the present invention.

In one embodiment, the ophthalmic compositions of the present invention will contain ethanol in addition to a compound of formula (I). As used herein, "an effective concentration of ethanol" refers to a concentration that enhances the biological efficacy of the formula (I) compositions in vivo. In general, the concentration of ethanol necessary for the enhancement of the compounds of formula (I) is believed to be somewhat proportional to the concentration of the formula (I) compound(s) administered. If a relatively high concentration of formula (I) compound(s), e.g., above 0.01% w/v, is administered, the concentration of ethanol in such compositions may be proportionally less than analogous compositions containing lower concentrations of formula (I) compounds. In general, however, the ethanol concentration contained in the ophthalmic compositions of the present invention will range from about 0.001–2% w/v. Compositions containing formula (I) concentrations of about 0.00001–0.02% w/v preferably will contain ethanol in a concentration of about 0.005–0.2% w/v, and most preferably, about 0.02–0.10% w/v. An example of a topically administrable ophthalmic formulation according to this embodiment of the present invention is provided below.

EXAMPLE 20

| Ingredient | Amount (% w/v) |
| --- | --- |
| Compound of formula (I) | 0.00001–0.01 |
| Ethanol | 0.0505 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method. The batch quantities of polyoxyl 40 stearate, boric acid, sodium chloride, disodium edetate, and polyquaternium-1 are weighed and dissolved by stirring in 90% of the batch quantity of purified water. The pH is adjusted to 7.5±0.1 with NaOH and/or HCl. Under yellow light or reduced lighting, the batch quantity of a compound of formula (I) as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A composition for the treatment of dry eye in humans comprising a pharmaceutically acceptable carrier and a pharmaceutically effective amount of one or more compounds of the following formula I:

$$n\text{-}C_5H_{11}\text{—}Y\text{—}A\text{—}CH_2\text{—}R^1 \qquad \text{I}$$

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:
  R is H or a pharmaceutically acceptable cation, or $CO_2R$ forms a pharmaceutically acceptable ester moiety;
  $NR^2R^3$, $NR^5R^6$ are the same or different and comprise a free or functionally modified amino group;
  $OR^4$ comprises a free or functionally modified hydroxy group;
  Hal is F, Cl, Br, or I;
  $R^{20}$ is H, alkyl, acyl;
  $R^{21}$ is H or a pharmaceutically acceptable cation, or $COSR^{21}$ forms a pharmaceutically acceptable thioester moiety;
A is $L_1$—$A_1$—$L_2$, $L_1$—$A_2$—$L_2$, $L_3$—$A_2$—$L_4$, or $L_5$—$A_2$—$L_3$;
$A_1$ is $CH_2CH_2$;
$A_2$ is

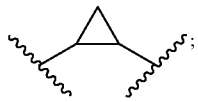

$L_1$ is $CH_2$—B—D;
B and D are the same or different and are $CH_2CH_2$, CH=CH, or C≡C;
$L_2$ is $CH_2$—K—$CH_2CH_2$;
K is $CH_2CH_2$, CH=CH, or C≡C;
$L_3$ is $CH_2CH_2CH_2$, $CH_2$CH=CH, $CH_2$C≡C, CH=CHCH$_2$, C≡CCH$_2$, or CH=C=CH;
$L_4$ is X—$CH_2CH_2$;
X is $CH_2CH_2$CH=CH, $CH_2CH_2$C≡C, $CH_2CH_2CH_2CH_2$, $CH_2$CH=CHCH$_2$, $CH_2$C≡CCH$_2$, CH=CHCH$_2$CH$_2$, C≡CCH$_2$CH$_2$, $CH_2$CH=C=CH, or CH=C=CHCH$_2$;
$L_5$ is $CH_2CH_2$—B—D; and
Y is C(O) (i.e. a carbonyl group) or Y is

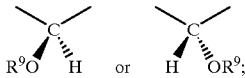

wherein $R^9O$ constitutes a free or functionally modified hydroxy group.

2. The composition of claim 1, wherein for the compound of formula I:
$R^1$ is $CO_2R$, where R is H or an ophthalmically acceptable cationic salt, or $CO_2R$ forms an ophthalmically acceptable ester moiety;
A is $L_1$—$A_1$—$L_2$ or $L_1$—$A_2$—$L_2$;
$A_1$ is $CH_2CH_2$;
$A_2$ is

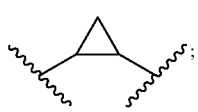

$L_1$ is $CH_2$—B—D;
$L_2$ is $CH_2$—K—$CH_2CH_2$;
B is C≡C or cis-CH=CH and D is C≡C or trans-CH=CH;
K is cis-CH=CH; and
Y is

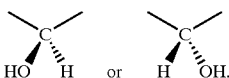

3. The composition of claim 2, wherein the compound is selected from the group consisting of:

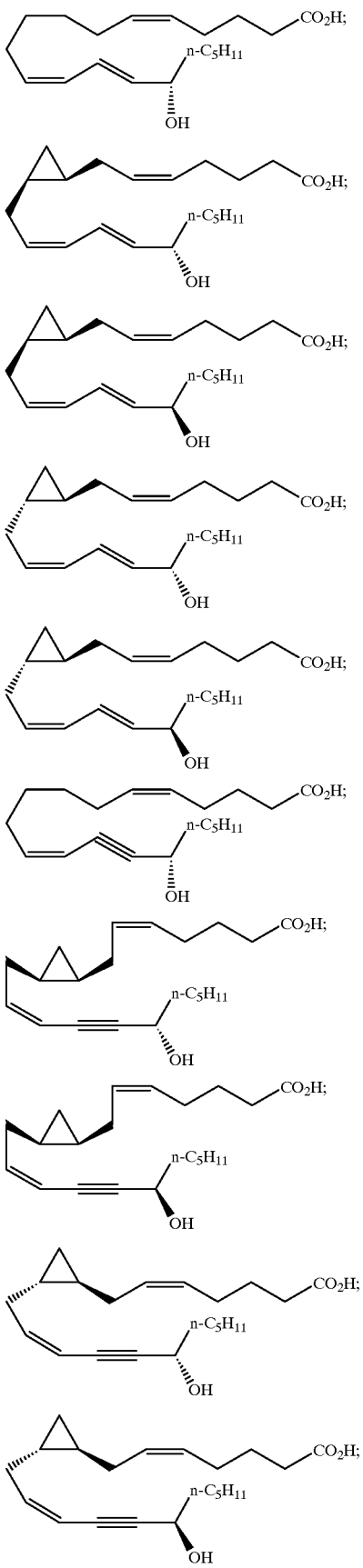

-continued

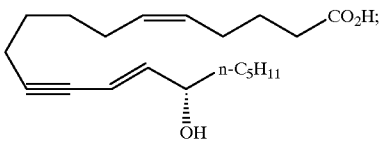

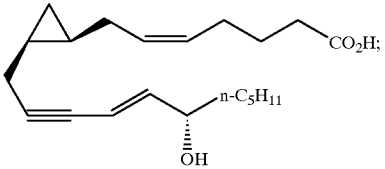

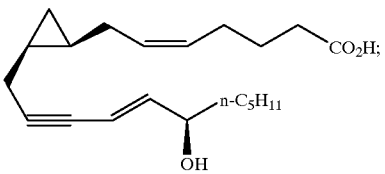

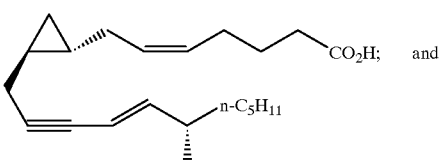   and

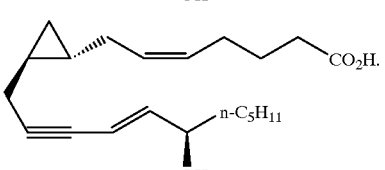

4. The composition of claim 1, wherein for the compound of formula I:

$R^1$ is $CO_2R$, where R is H or an ophthalmically acceptable cationic salt, or $CO_2R$ forms an ophthalmically acceptable ester moiety;

A is $L_3$—$A_2$—$L_4$;

$A_2$ is

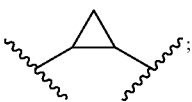

$L_3$ is trans-$CH_2CH$=$CH$, trans-$CH$=$CHCH_2$, or $CH_2C$≡$C$;

$L_4$ is X—$CH_2CH_2$;

X is cis-$CH_2CH_2CH$=$CH$, $CH_2CH_2C$≡$C$, cis-$CH_2CH$=$CHCH_2$, or cis-$CH$=$CHCH_2CH_2$; and Y is

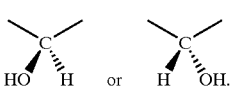

5. The composition of claim 4, wherein the compound of formula I is selected from the group consisting of:

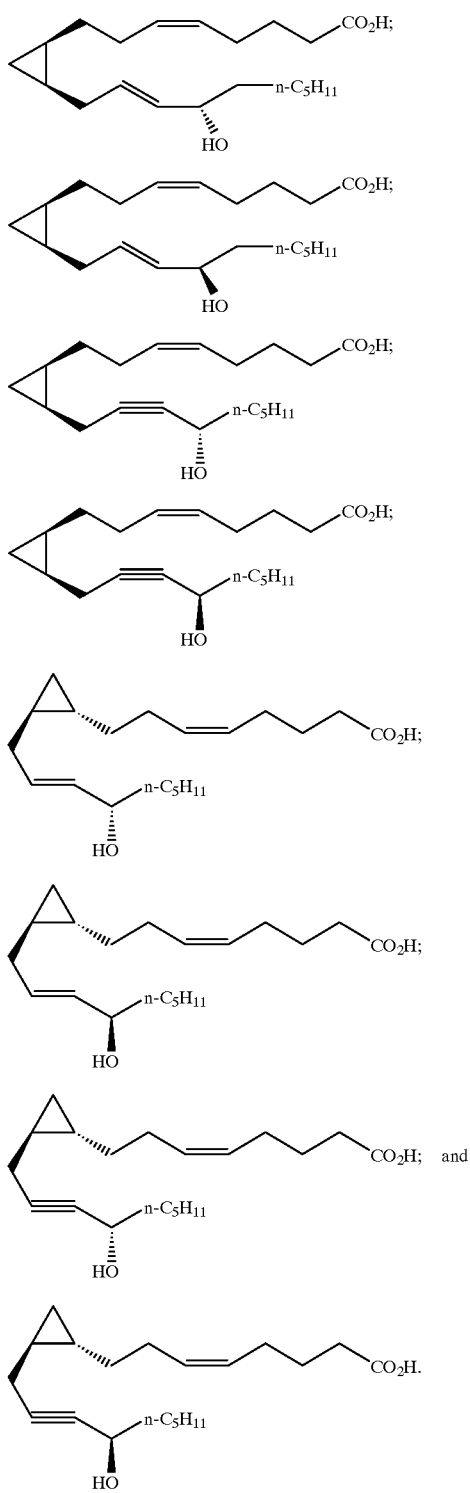

6. The composition of claim 1, wherein for the compound of formula I:

$R^1$ is $CO_2R$, where R is H or an ophthalmically acceptable cationic salt, or $CO_2R$ forms an ophthalmically acceptable ester moiety;

A is $L_5$—$A_2$—$L_3$;

$A_2$ is

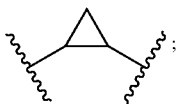

$L_5$ is $CH_2CH_2$—B—D;
$L_3$ is cis-$CH_2CH$=CH, cis-CH=$CHCH_2$, $CH_2C$≡C, or $CH_2CH_2CH_2$;
B is cis-CH=CH or C≡C;
D is trans-CH=CH or C≡C; and
Y is

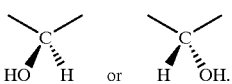

7. The composition of claim 6, wherein the compound is selected from the group consisting of:

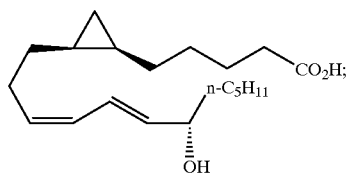

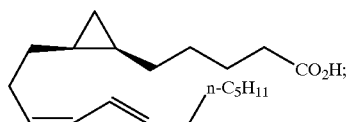

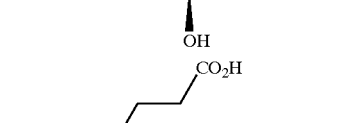

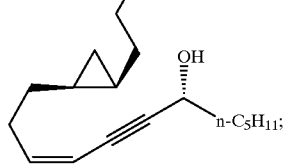

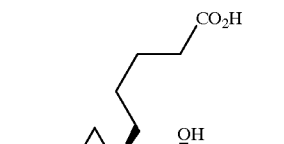

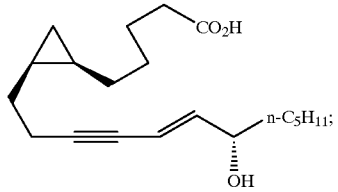

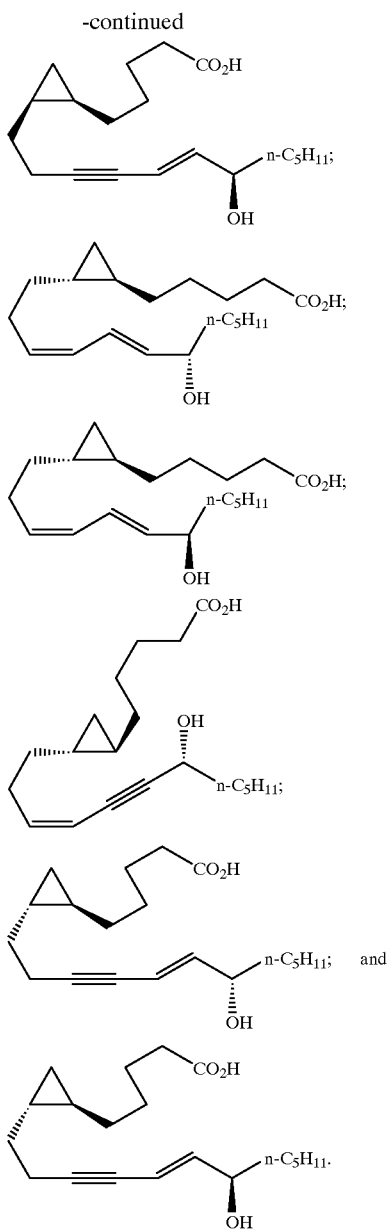

8. The composition of claim 1, wherein the composition is a suitable for topical administration to the eye.

9. A method for the treatment of dry eye or other disorders requiring the wetting of the eye in mammals comprising administering to an affected eye, a pharmaceutically effective amount of one or more compounds according to formula I:

$$n\text{-}C_5H_{11}\text{—}Y\text{—}A\text{—}CH_2\text{—}R^1 \qquad I$$

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:
  R is H or a pharmaceutically acceptable cation, or $CO_2R$ forms a pharmaceutically acceptable ester moiety;
  $NR^2R^3$, $NR^5R^6$ are the same or different and comprise a free or functionally modified amino group;
  $OR^4$ comprises a free or functionally modified hydroxy group;
  Hal is F, Cl, Br, or I;
  $R^{20}$ is H, alkyl, acyl;
  $R^{21}$ is H or a pharmaceutically acceptable cation, or $COSR^{21}$ forms a pharmaceutically acceptable thioester moiety;

A is $L_1$—$A_1$—$L_2$, $L_1$—$A_2$—$L_2$, $L_3$—$A_2$—$L_4$, or $L_5$—$A_2$—$L_3$;

$A_1$ is $CH_2CH_2$;

$A_2$ is

$L_1$ is $CH_2$—B—D;

B and D are the same or different and are $CH_2CH_2$, CH=CH, or C≡C;

$L_2$ is $CH_2$—K—$CH_2CH_2$;

K is $CH_2CH_2$, CH=CH, or C≡C;

$L_3$ is $CH_2CH_2CH_2$, $CH_2CH$=CH, $CH_2C$≡C, CH=CHCH_2, C≡CCH_2, or CH=C=CH;

$L_4$ is X—$CH_2CH_2$;

X is $CH_2CH_2CH$=CH, $CH_2CH_2C$≡C, $CH_2CH_2CH_2CH_2$, $CH_2CH$=CHCH_2, $CH_2C$≡CCH_2, CH=CHCH_2CH_2, C≡CCH_2CH_2, $CH_2CH$=C=CH, or CH=C=CHCH_2;

$L_5$ is $CH_2CH_2$—B—D; and

Y is C(O) (i.e. a carbonyl group) or Y is

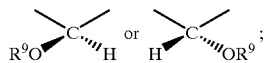

wherein $R^9O$ constitutes a free or functionally modified hydroxy group.

10. The method of claim 9, wherein the mammal is a human and the compound is administered topically.

11. The method of claim 9, wherein for the compound of formula I:

$R^1$ is $CO_2R$, where R is H or an ophthalmically acceptable cationic salt, or $CO_2R$ forms an ophthalmically acceptable ester moiety;

A is $L_1$—$A_1$—$L_2$ or $L_1$—$A_2$—$L_2$;

$A_1$ is $CH_2CH_2$;

$A_2$ is

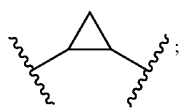

$L_1$ is $CH_2$—B—D;

$L_2$ is $CH_2$—K—$CH_2CH_2$;

B is C≡C or cis-CH=CH and D is C≡C or trans-CH=CH;

K is cis-CH=CH; and

Y is

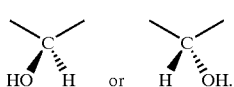

12. The method of claim 11, wherein the compound is selected from the group consisting of:

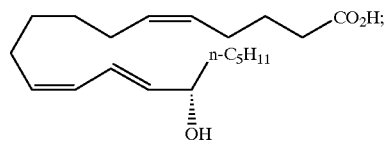

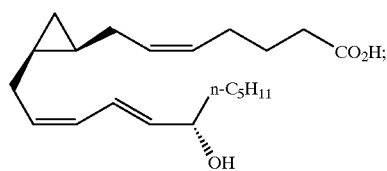

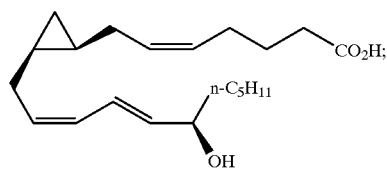

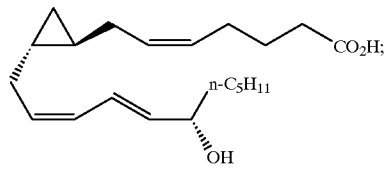

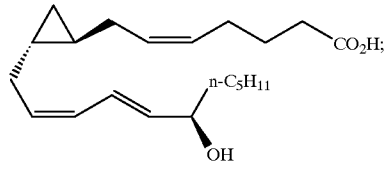

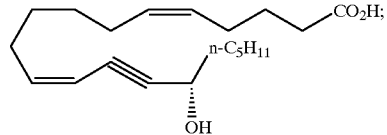

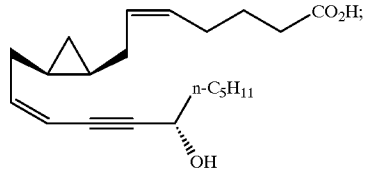

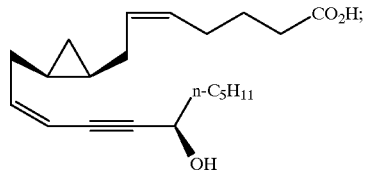

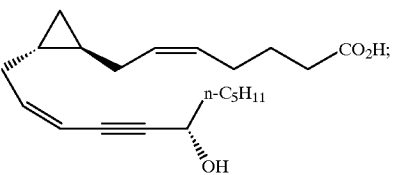

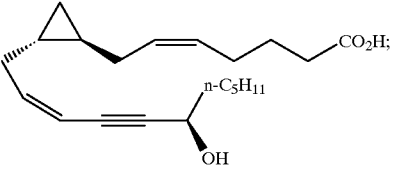

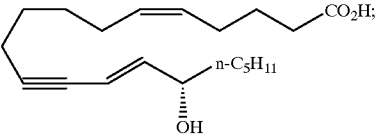

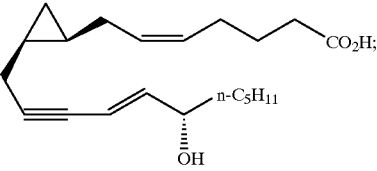

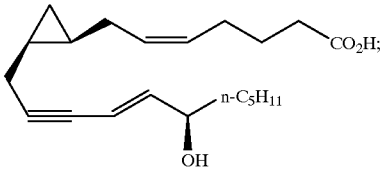

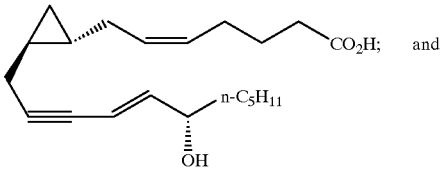

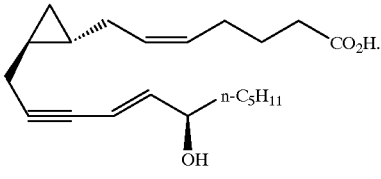

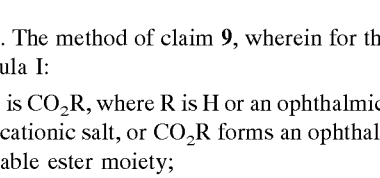

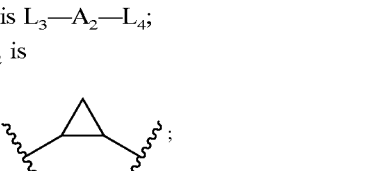

13. The method of claim 9, wherein for the compound of formula I:

$R^1$ is $CO_2R$, where R is H or an ophthalmically acceptable cationic salt, or $CO_2R$ forms an ophthalmically acceptable ester moiety;

A is $L_3$—$A_2$—$L_4$;

$A_2$ is

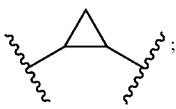

$L_3$ is trans-$CH_2CH{=}CH$, trans-$CH{=}CHCH_2$, or $CH_2C{\equiv}C$;

$L_4$ is X—$CH_2CH_2$;

X is cis-CH$_2$CH$_2$CH=CH, CH$_2$CH$_2$C≡C, cis-CH$_2$CH=CHCH$_2$, or cis-CH=CHCH$_2$CH$_2$; and
Y is

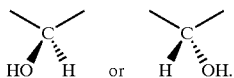

14. The method of claim 13, wherein the compound is selected from the group consisting of:

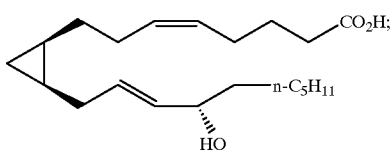

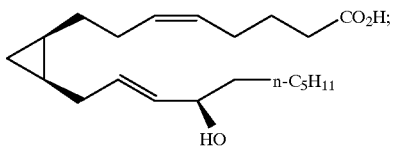

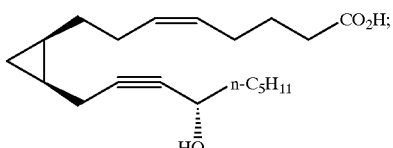

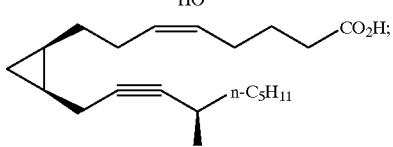

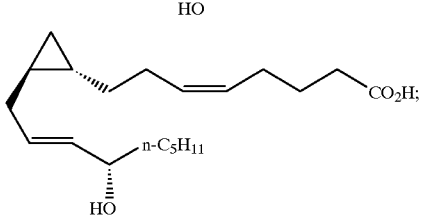

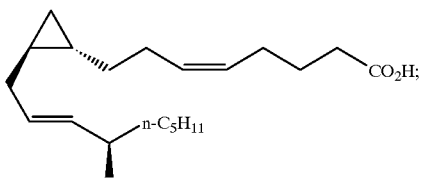

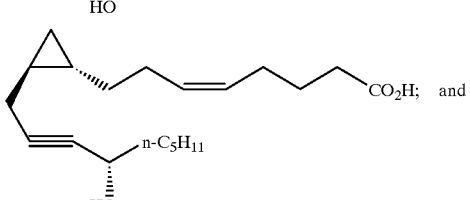

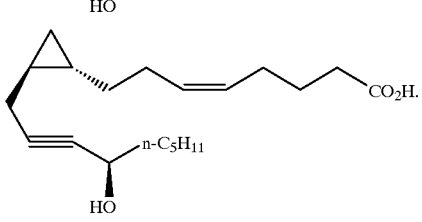

15. The method of claim 9, wherein for the compound of formula I:

R$^1$ is CO$_2$R, where R is H or an ophthalmically acceptable cationic salt, or CO$_2$R forms an ophthalmically acceptable ester moiety;

A is L$_5$—A$_2$—L$_3$;

A$_2$ is

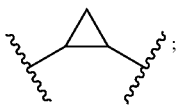

L$_5$ is CH$_2$CH$_2$—B—D;

L$_3$ is cis-CH$_2$CH=CH, cis-CH=CHCH$_2$, CH$_2$C≡C, or CH$_2$CH$_2$CH$_2$

B is cis-CH=CH or C≡C;

D is trans-CH=CH or C≡C; and

Y is

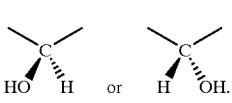

16. The method of claim 15, wherein the compound is selected from the group consisting of:

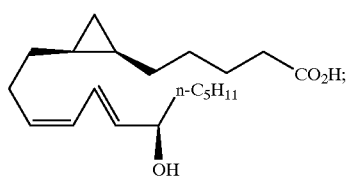

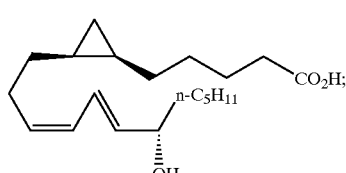

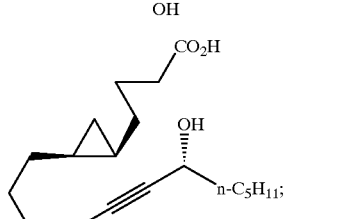

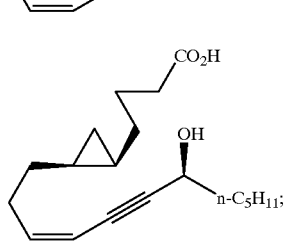

17. The method of claim 9 wherein the dry eye and other disorders requiring the wetting of the eye is symptoms of dry eye associated with refractive surgery.

18. A compound of formula I:

$$n\text{-}C_5H_{11}\text{—}Y\text{—}A\text{—}CH_2\text{—}R^1 \qquad \text{I}$$

wherein:

$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:

R is H or a pharmaceutically acceptable cation, or $CO_2R$ forms a pharmaceutically acceptable ester moiety;

$NR^2R^3$, $NR^5R^6$ are the same or different and comprise a free or functionally modified amino group;

$OR^4$ comprises a free or functionally modified hydroxy group;

Hal is F, Cl, Br, or I;

$R^{20}$ is H, alkyl, acyl;

$R^{21}$ is H or a pharmaceutically acceptable cation, or $COSR^{21}$ forms a pharmaceutically acceptable thioester moiety; A is $L_1$—$A_2$—$L_2$, $L_3$—$A_2$—$L_4$, or $L_5$—$A_2$—$L_3$;

$A_2$ is $L_1$ is $CH_2$—B—D;

B and D are the same or different and are $CH_2CH_2$, CH=CH, or C≡C;

$L_2$ is $CH_2$—K—$CH_2CH_2$;

K is $CH_2CH_2$, CH=CH, or C≡C;

$L_3$ is $CH_2CH_2CH_2$, $CH_2$CH=CH, $CH_2$C≡C, CH=CHCH$_2$, C≡CCH$_2$, or CH=C=CH;

$L_4$ is X—$CH_2CH_2$;

X is $CH_2CH_2$CH=CH, $CH_2CH_2$C≡C, $CH_2CH_2CH_2CH_2$, $CH_2$CH=CHCH$_2$, $CH_2$C≡CCH$_2$, CH=CHCH$_2$CH$_2$, C≡CCH$_2$CH$_2$, $CH_2$CH=C=CH, or CH=C=CHCH$_2$;

$L_5$ is $CH_2CH_2$—B—D; and

Y is C(O) (i.e. a carbonyl group) or Y is wherein $R^9O$ constitutes a free or functionally modified hydroxy group.

19. The compound of claim 18, wherein:

$R^1$ is $CO_2R$, where R is H or an ophthalmically acceptable cationic salt, or $CO_2R$ forms an ophthalmically acceptable ester moiety;

A is $L_1$—$A_2$—$L_2$;

$A_2$ is $L_1$ is $CH_2$—B—D;

$L_2$ is $CH_2$—K—$CH_2CH_2$;

B is C≡C or cis-CH=CH and D is C≡C or trans-CH=CH;

K is cis-CH=CH; and

Y is

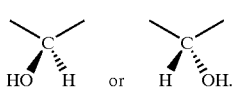 or

20. The compound of claim 19, wherein the compound is selected from the group consisting of:

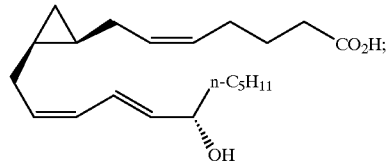

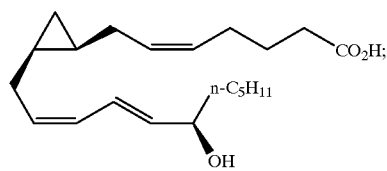

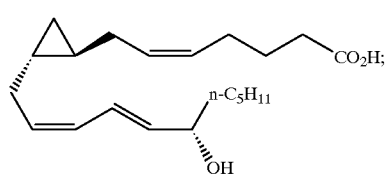

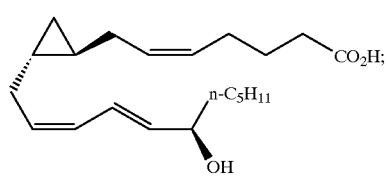

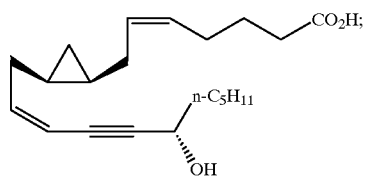

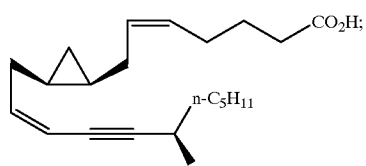

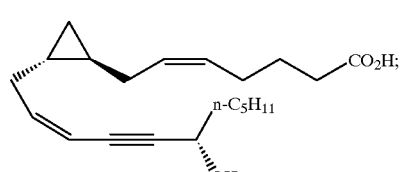

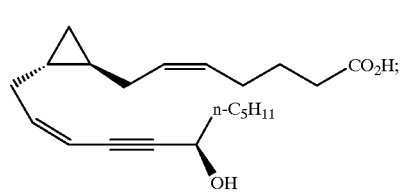

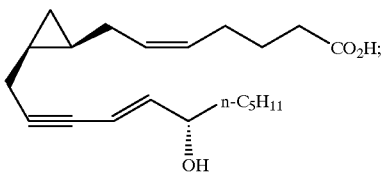

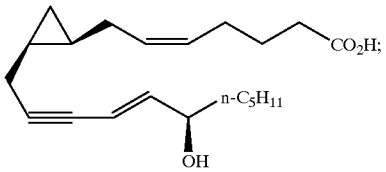

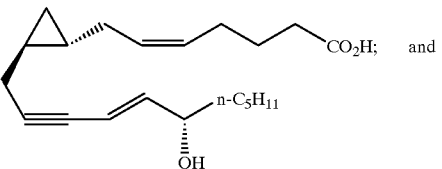 and

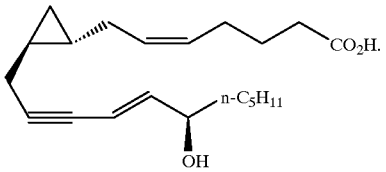

21. The compound of claim 18, wherein:

$R^1$ is $CO_2R$, where R is H or an ophthalmically acceptable cationic salt, or $CO_2R$ forms an ophthalmically acceptable ester moiety;

A is $L_3$—$A_2$—$L_4$;

$A_2$ is

;

$L_3$ is trans-$CH_2CH=CH$, trans-$CH=CHCH_2$, or $CH_2C\equiv C$;

$L_4$ is X—$CH_2CH_2$;

X is cis-$CH_2CH_2CH=CH$, $CH_2CH_2C\equiv C$, cis-$CH_2CH=CHCH_2$, or cis-$CH=CHCH_2CH_2$; and Y is

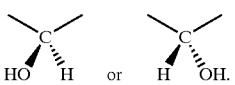

22. The compound of claim 21, wherein the compound is selected from the group consisting of:

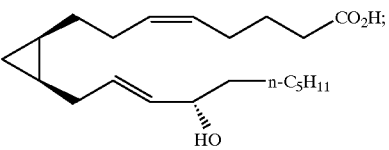

-continued

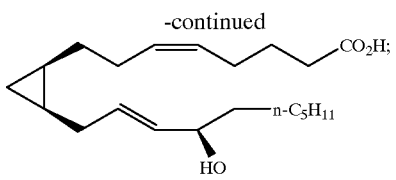
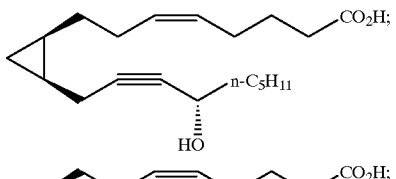
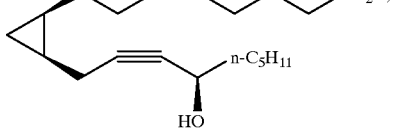
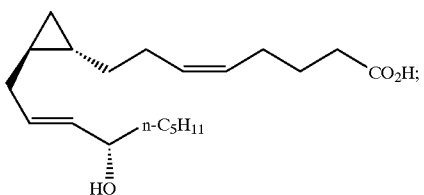
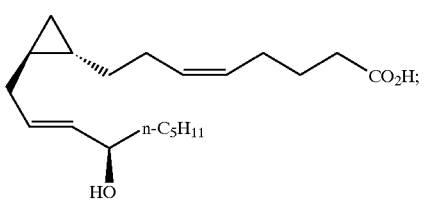
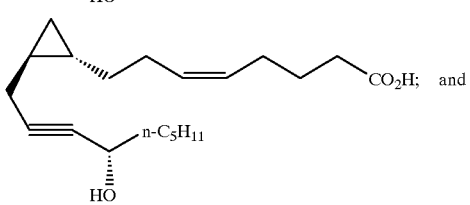
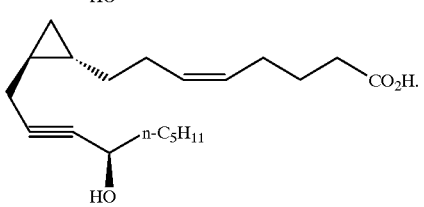

23. The compound of claim 18, wherein:
$R^1$ is $CO_2R$, where R is H or an ophthalmically acceptable cationic salt, or $CO_2R$ forms an ophthalmically acceptable ester moiety;
is A is $L_5$—$A_2$—$L_3$;
$A_2$ is

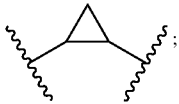

$L_5$ is $CH_2CH_2$—B—D;
$L_3$ is cis-$CH_2CH=CH$, cis-$CH=CHCH_2$, $CH_2C\equiv C$, or $CH_2CH_2CH_2$;
B is cis-$CH=CH$ or $C\equiv C$;

D is trans-$CH=CH$ or $C\equiv C$; and
Y is

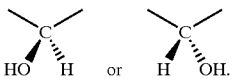

24. The compound of claim 23, wherein the compound is selected from the group consisting of:

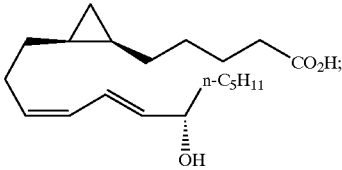
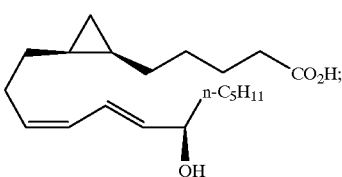
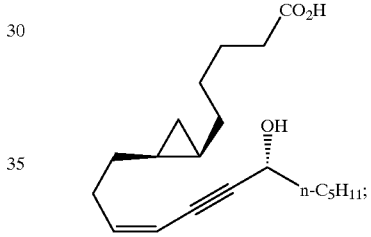
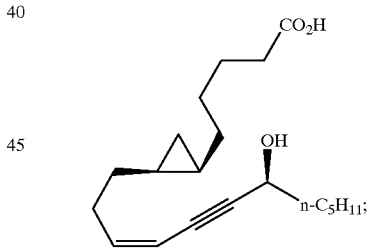
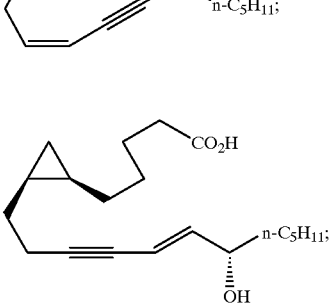
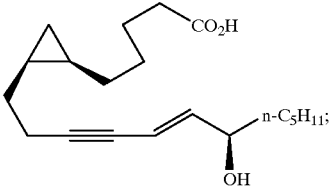

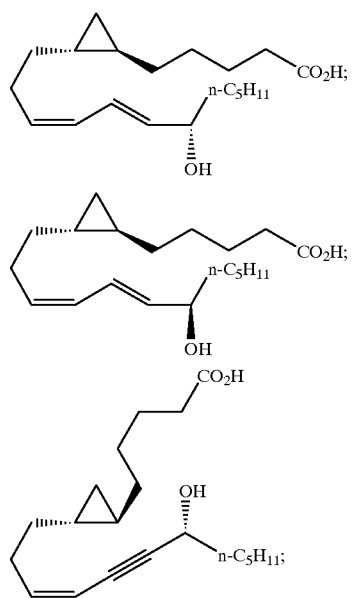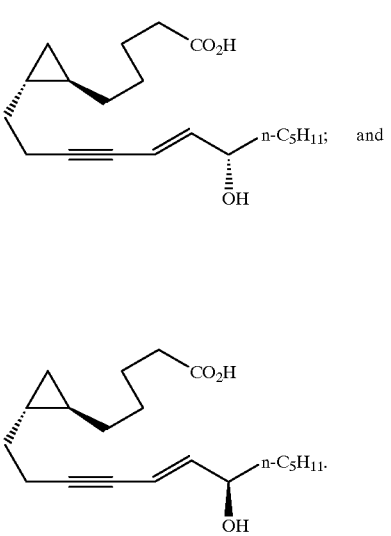
* * * * *